United States Patent
Hanson et al.

(10) Patent No.: US 9,326,708 B2
(45) Date of Patent: May 3, 2016

(54) AMBIENT TEMPERATURE SENSOR SYSTEMS AND METHODS

(75) Inventors: Ian B. Hanson, Northridge, CA (US); Dore Mark, San Jose, CA (US); Sean Daley, San Jose, CA (US); Sheldon B. Moberg, Thousand Oaks, CA (US); Susie E. Buckman, Torrance, CA (US); Paul F. Bente, IV, South Pasadena, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 847 days.

(21) Appl. No.: 12/748,239

(22) Filed: Mar. 26, 2010

(65) Prior Publication Data

US 2011/0237916 A1    Sep. 29, 2011

(51) Int. Cl.
*A61B 5/00*      (2006.01)
*A61B 5/145*      (2006.01)

(52) U.S. Cl.
CPC ........... *A61B 5/14532* (2013.01); *A61B 5/0008* (2013.01)

(58) Field of Classification Search
CPC .......................... A61B 5/14532; A61B 5/0008
USPC .................. 600/365, 319, 316, 331, 332, 347
See application file for complete search history.

(56) References Cited

U.S. PATENT DOCUMENTS

| | | | | |
|---|---|---|---|---|
| 5,405,511 A | * | 4/1995 | White et al. | 205/777.5 |
| 6,880,968 B1 | * | 4/2005 | Haar | 374/131 |
| 8,614,097 B2 | * | 12/2013 | Blais et al. | 436/147 |
| 8,617,381 B2 | * | 12/2013 | Sun | A61B 5/01 204/400 |
| 2003/0100821 A1 | * | 5/2003 | Heller et al. | 600/347 |
| 2006/0229502 A1 | | 10/2006 | Pollock et al. | |
| 2010/0130838 A1 | * | 5/2010 | Kermani et al. | 600/310 |

FOREIGN PATENT DOCUMENTS

WO    WO-2010/032911 A1    3/2010

OTHER PUBLICATIONS

International Search Report dated Apr. 21, 2011 from related PCT Application No. PCT/US2011/024929.

* cited by examiner

*Primary Examiner* — Michael Kahelin
*Assistant Examiner* — Tho Tran
(74) *Attorney, Agent, or Firm* — Foley & Lardner LLP

(57) ABSTRACT

A first sensor may be configured to measure a sensed amount of a physiological parameter and to generate a first signal based on the sensed amount of the physiological parameter measured by the first sensor. A second sensor may be configured to measure a temperature and to generate a second signal based on the temperate measured by the second sensor. A housing may have heat-generating electronics including a processor that may be configured to determine an overall amount of the physiological parameter based on the first signal generated from the first sensor and the second signal generated from the second sensor. The second sensor may be thermally insulated from the heat-generating electronics.

40 Claims, 18 Drawing Sheets

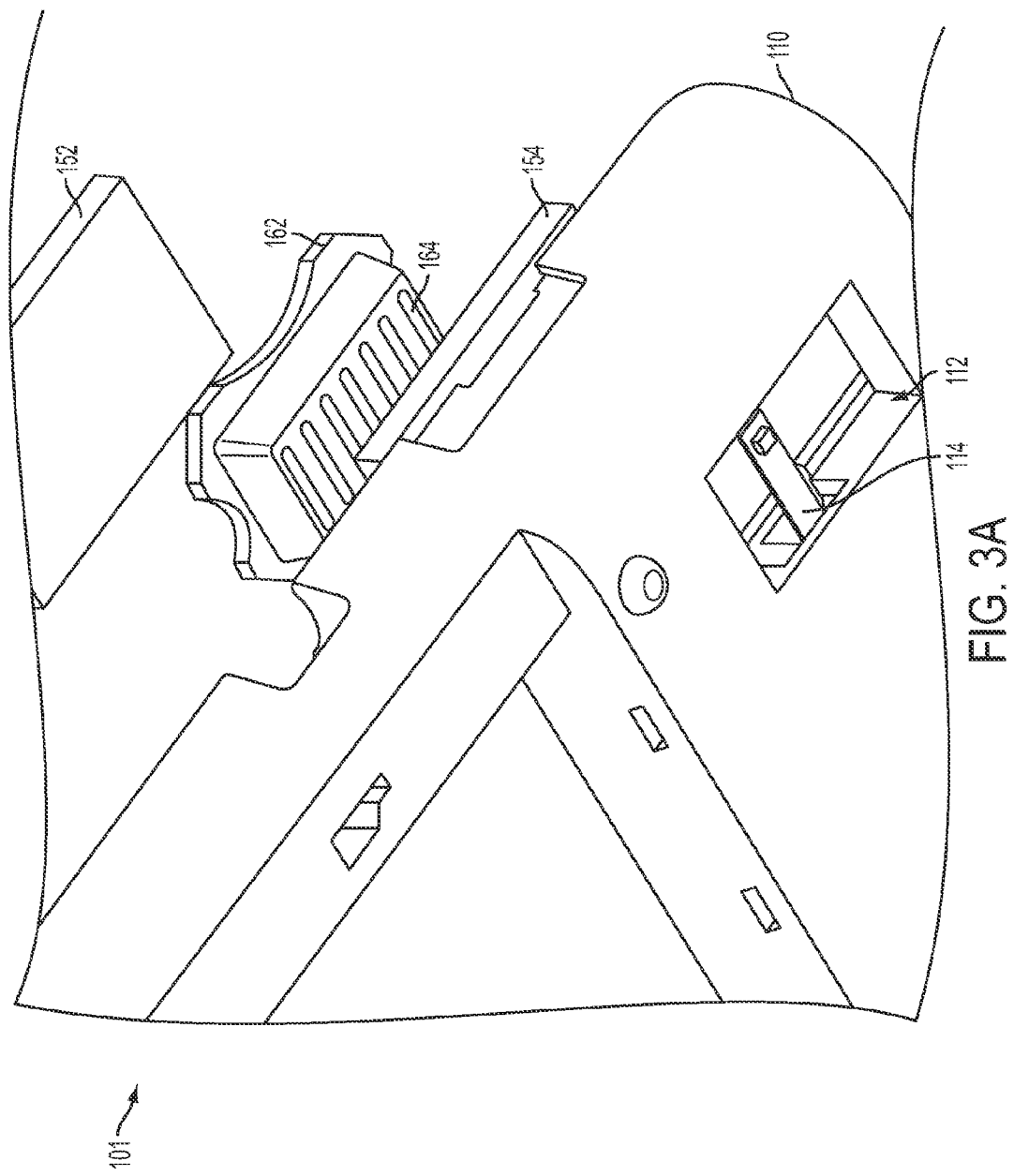

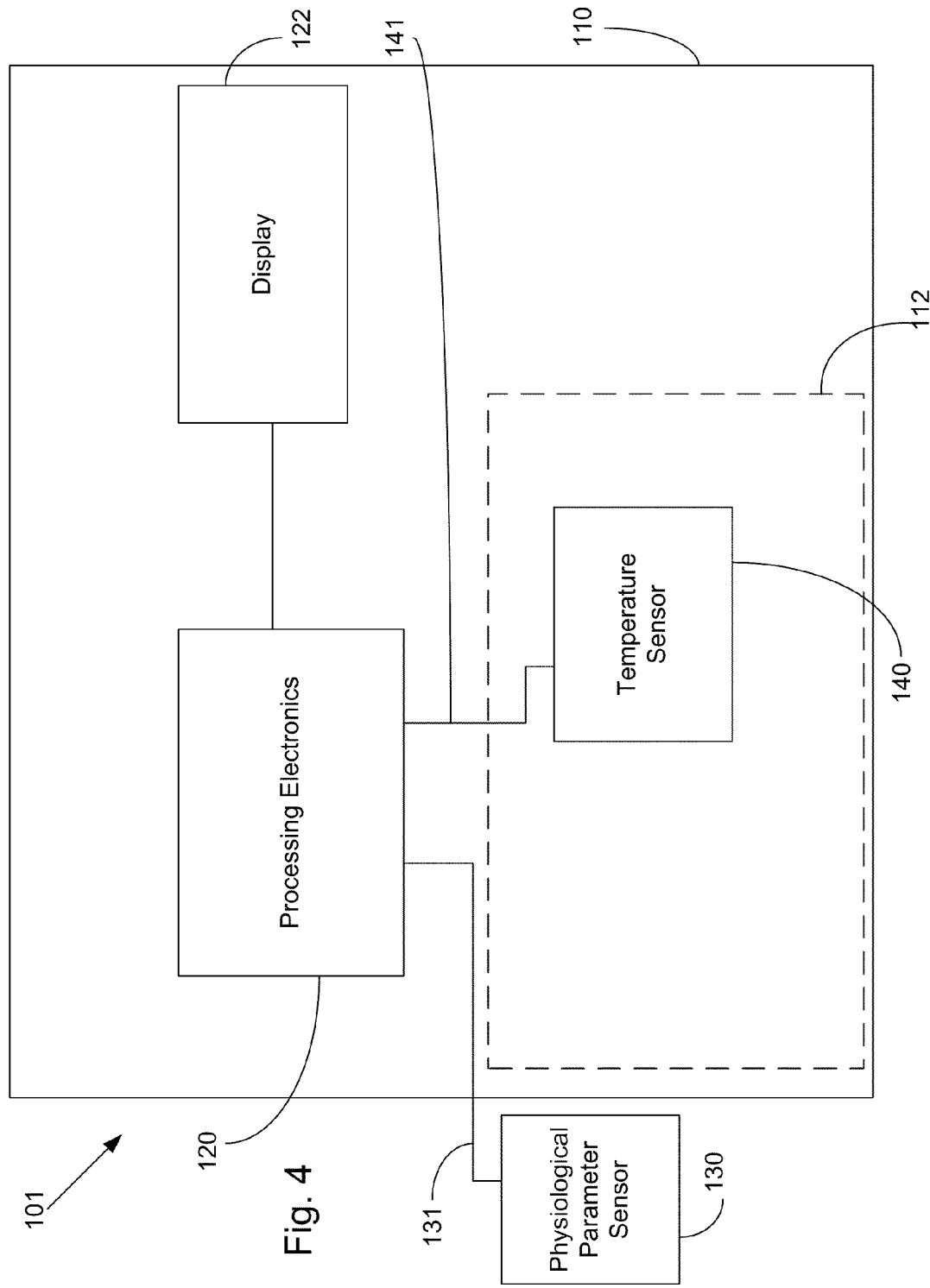

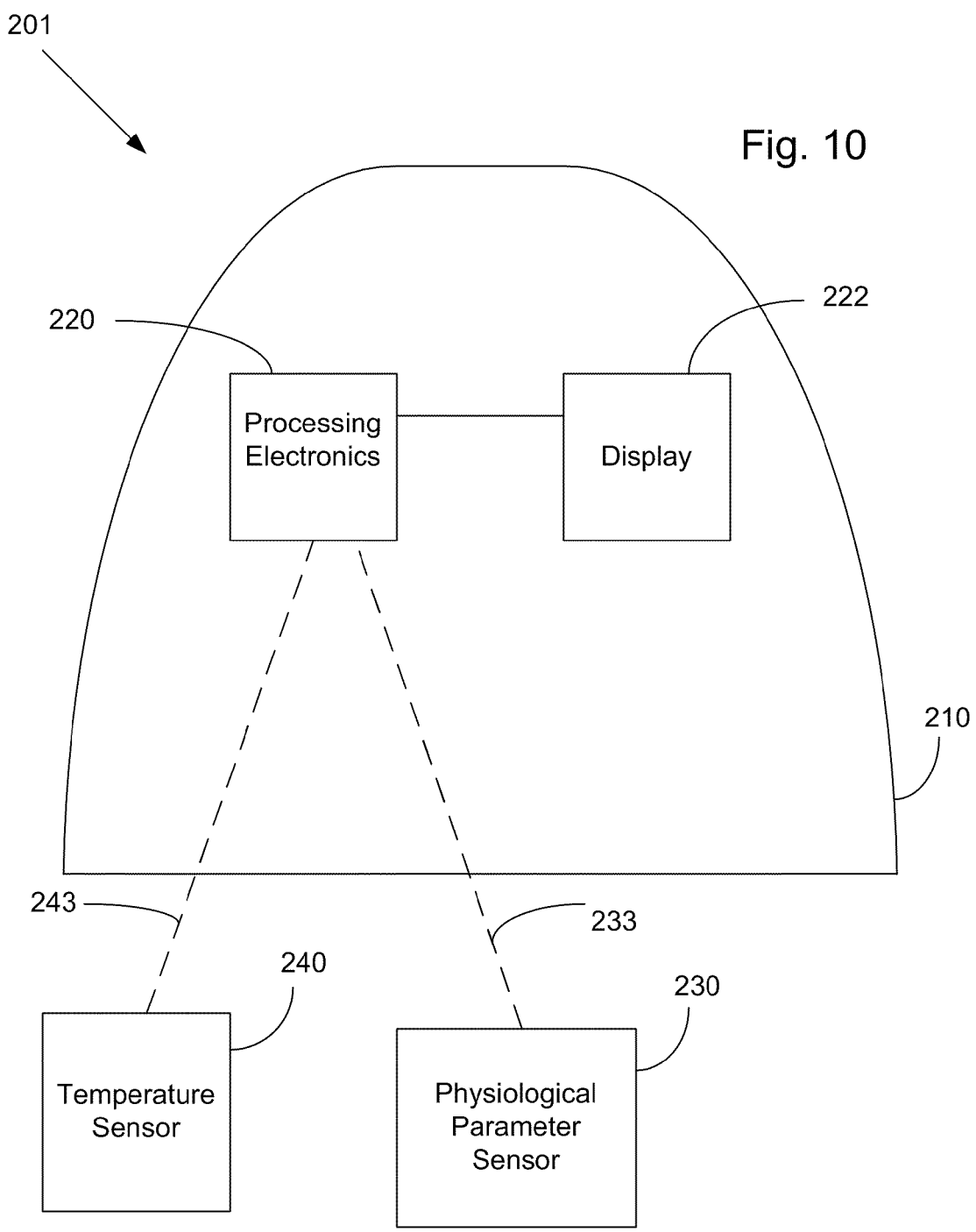

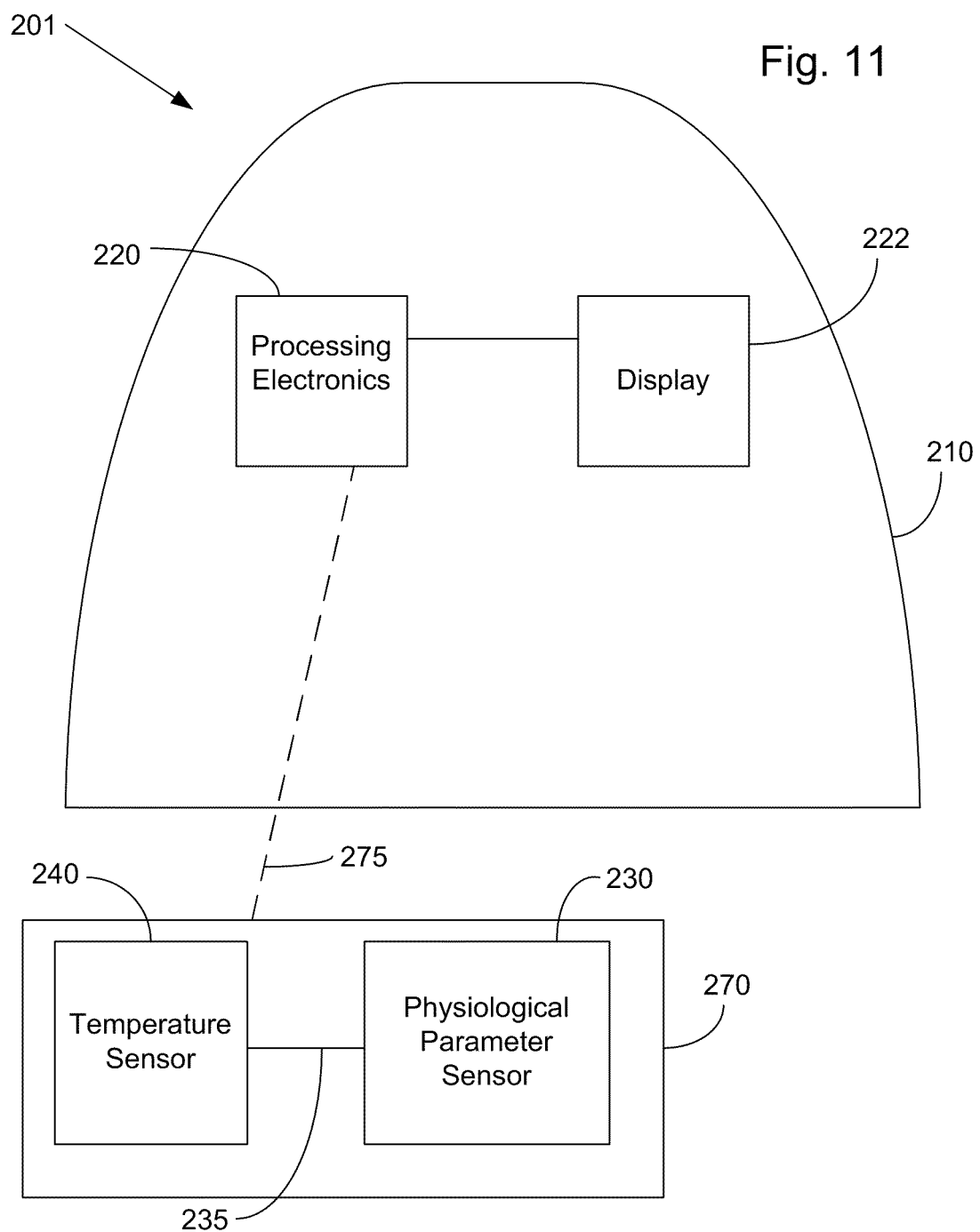

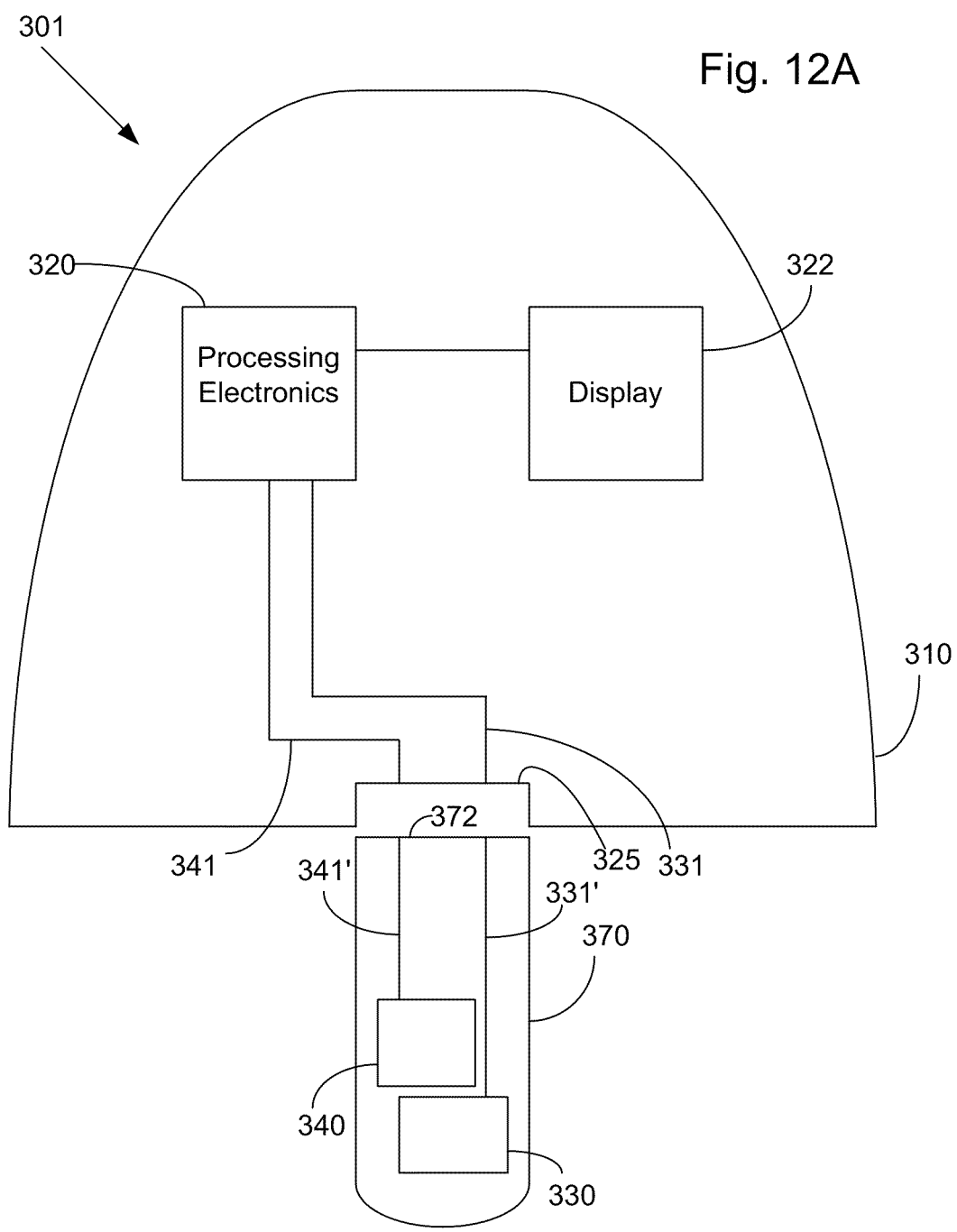

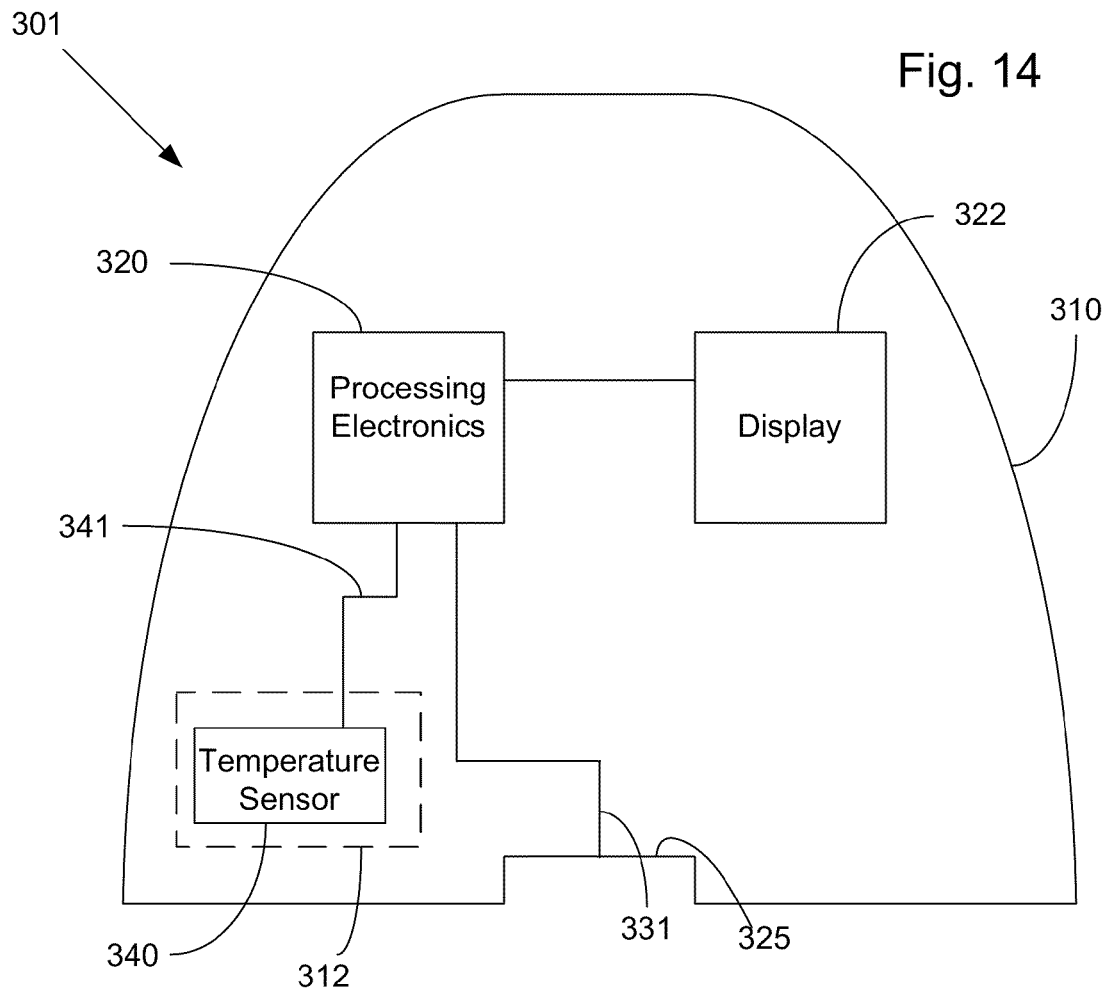
Fig. 14
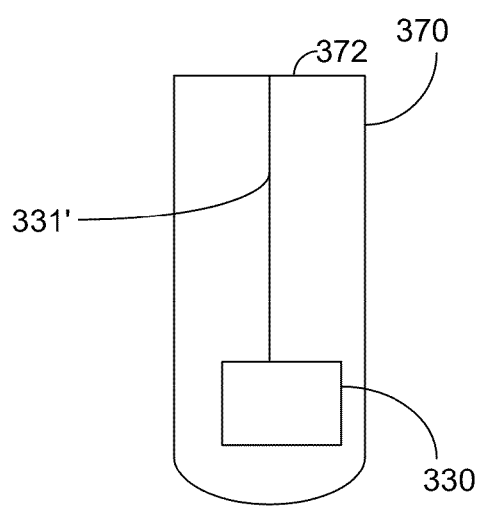

AMBIENT TEMPERATURE SENSOR SYSTEMS AND METHODS

BACKGROUND OF THE INVENTION

1. Field of the Invention

Embodiments of the present invention relate generally to systems and methods that include monitoring devices having sensors and, in specific embodiments, to systems and methods for monitoring devices with temperature and physiological parameter sensors.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a user-patient, for example, through suitable hollow tubing. The hollow tubing may be connected to a hollow needle that is designed to pierce the user-patient's skin and deliver an infusion medium to the user-patient. Alternatively, the hollow tubing may be connected directly to the user-patient as or through a cannula or set of micro-needles.

In contexts in which the hollow tubing is connected to the user-patient through a hollow needle that pierces skin of the user-patient, a manual insertion of the needle into the user-patient can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211, 095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Pump-type delivery devices can allow accurate doses of insulin to be calculated and delivered automatically to a user-patient at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and user-patients become more familiar with such devices, the popularity of external medical infusion pump treatment increases and is expected to increase substantially over the next decade.

SUMMARY OF THE DISCLOSURE

A monitoring system for measuring a physiological parameter may include, but is not limited to, a housing, a first sensor, and a second sensor. The housing may have heat-generating electronics. The first sensor may be configured to measure a sensed amount of a physiological parameter and to generate a first signal based on the sensed amount of the physiological parameter measured by the first sensor. The second sensor may be configured to measure a temperature and to generate a second signal based on the temperate measured by the second sensor. The heat-generating electronics may comprise a processor that may be configured to determine an overall amount of the physiological parameter based on the first signal generated from the first sensor and the second signal generated from the second sensor. The second sensor may be thermally insulated from the heat-generating electronics.

In various embodiments, the physiological parameter may comprise a concentration of blood glucose. In various embodiments, the system may include a thermal insulation material surrounding at least a portion of the second sensor. The thermal insulation material may be adapted to thermally insulate the second sensor from heat generated by the heat-generating electronics. In various embodiments, the system may include a thermal insulation material surrounding at least a portion of the second sensor. The thermal insulation material may be adapted to thermally insulate the second sensor from air external the housing.

In various embodiments, the housing may have a chamber. The second sensor may be arranged within the chamber. The chamber may be sufficiently located from the heat-generating electronics to minimize an affect of the heat-generating electronics on the temperature measured by the second sensor. In some embodiments, the chamber may be located at a location corresponding to approximately a furthest distance within the housing from the heat-generating electronics. In some embodiments, the chamber may be located at a location corresponding to approximately a coolest portion of the housing during operation of the monitoring system.

In various embodiments, the system may include a structure and a thermal insulation material. The structure may be for supporting the second sensor. The thermal insulation material may be surrounding at least a portion of the second sensor. The thermal insulation material may be adapted to thermally insulate the second sensor from at least one of heat generated by the heat-generating electronics and air external the housing. The housing may have a chamber. The structure may be arranged within the chamber of the housing.

In various embodiments, the second sensor may be arranged external to the housing. In some embodiments, the second sensor may be attached to an external surface of the housing. In some embodiments, the second sensor may be located separate and spaced apart from the housing.

In various embodiments, the first sensor may be arranged within the housing. In various embodiments, the first sensor may be configured to measure the sensed amount of the physiological parameter at a location having a local temperature. The second sensor may be adapted to be positioned relative to the housing at a location at which the temperature measured by the second sensor is closer to the local temperature than a temperature of a heat source emitted by the heat-generating electronics.

In various embodiments, the second sensor may comprise a temperature sensor. In various embodiments, the system may include a heat-conductive material adapted to transfer heat away from at least one of a portion of the housing containing the heat-generating electronics and a portion of the housing containing the second sensor to raise or lower a temperature within the housing measured by the second sensor. In some embodiments, the heat-conductive material may comprise a heat sink.

In various embodiments, the system may include a heat-conductive material adapted to transfer ambient temperature to at least one of a portion of the housing containing the heat-generating electronics and a portion of the housing containing the second sensor to raise or lower a temperature within the housing measured by the second sensor. In various embodiments, the housing may have an opening for allowing air external to the housing to flow to at least one of a portion of the housing containing the heat-generating electronics and a portion of the housing containing the second sensor to raise or lower a temperature within the housing measured by the second sensor.

In various embodiments, the system may include a ventilation device for providing air external to the housing to at least one of a portion of the housing containing the heat-generating electronics and a portion of the housing containing the second sensor to raise or lower a temperature within the housing measured by the second sensor. In various embodiments, the system may include a ventilation device for transferring air away from within at least one of a portion of the housing containing the heat-generating electronics and a portion of the housing containing the second sensor to outside the housing to raise or lower a temperature within the housing measured by the second sensor.

In various embodiments, the heat-generating electronics may comprise a display device. In various embodiments, the processor may be configured to provide an indicator based upon at least one of the first signal exceeding a threshold range and the second signal exceeding a threshold range.

In various embodiments, the system may include a removable support structure for removable connection with the housing. The removable support structure may be supporting the first sensor. In some embodiments, the removable support structure may comprise a test strip.

In some embodiments, the removable support structure may be electronically connected to the housing when the removable support structure is connected to the housing. In some embodiments, the housing may have a receptacle for receiving at least a portion of the removable support structure and for providing an electrical connection for electrically connecting the removable support structure and the housing. In further embodiments, the portion of the removable support structure receivable by the receptacle may be an end of the removable support structure.

In some embodiments, the removable support structure may be supporting the second sensor. In some embodiments, the removable support structure may be configured to measure the sensed amount of the physiological parameter at a location along the removable support structure. The second sensor may be locatable at a position to be adjacent with the location on the removable support structure. In further embodiments, the housing may have a portion extending away from the housing. The second sensor may be located along the portion extending away from the housing to be adjacent with the location on the removable support structure.

In various embodiments, the housing may have a first portion extending away from the housing. The first sensor may be located at a position along the first portion. The housing may have a second portion extending away from the housing. The second sensor may be located at a position along the second portion. The first portion and the second portion may be arranged relative to each other such that the first sensor and the second sensor are adjacent each other.

In various embodiments, the second sensor may be sufficiently located from the heat-generating electronics to minimize an affect of the heat-generating electronics on the temperature measured by the second sensor. In some embodiments, the second sensor may be located at a location corresponding to approximately a furthest distance within the housing from the heat-generating electronics. In some embodiments, the second sensor may be located at a location corresponding to approximately a coolest portion of the housing during operation of the monitoring system.

A method of manufacturing a monitoring system for measuring a physiological parameter, may include, but is not limited to any one of or combination of: (i) providing a housing having heat-generating electronics; (ii) connecting a first sensor with the housing, the first sensor for measuring a sensed amount of a physiological parameter and for generating a first signal based on the sensed amount of the physiological parameter measured by the first sensor; (iii) arranging a second sensor to measure a temperature and for generating a second signal based on the temperate measured by the second sensor; (iv) determining an overall amount of the physiological parameter based on the first signal generated from the first sensor and the second signal generated from the second sensor; and (v) thermally insulating the second sensor from the heat-generating electronics.

A medical device for measuring a parameter may include, but is not limited to, a medical monitoring or treatment device, a parameter sensor, and a computing element. The medical monitoring or treatment device may be configured to provide a monitoring or treatment operation on a user. The medical monitoring or treatment device may be configured to receive a first signal from a parameter sensor configured to detect an amount of a physiological parameter. The first signal may be based on the amount of the physiological parameter detected by the parameter sensor. The temperature sensor may be configured to measure a temperature and to generate a second signal based on the temperature measured by the temperature sensor. The computing element may be configured to determine an overall amount of the physiological parameter based on the first signal and the second signal. The temperature sensor may be thermally insulated from heat produced within the medical monitoring or treatment device during use of the medical monitoring or treatment device.

BRIEF DESCRIPTION OF THE DRAWINGS

FIGS. 3A and 3B illustrate a monitoring device in accordance with an embodiment of the present invention;

FIG. 4 illustrates a block diagram of a monitoring device in accordance with an embodiment of the present invention;

FIG. 10 illustrates a block diagram of a monitoring device in accordance with an embodiment of the present invention;

FIG. 11 illustrates a block diagram of a monitoring device in accordance with an embodiment of the present invention;

FIGS. 12A and 12B illustrate a block diagram of a monitoring device in accordance with an embodiment of the present invention;

FIG. 14 illustrates a block diagram of a monitoring device in accordance with an embodiment of the present invention;

DETAILED DESCRIPTION OF THE PREFERRED EMBODIMENTS

Figure 1:
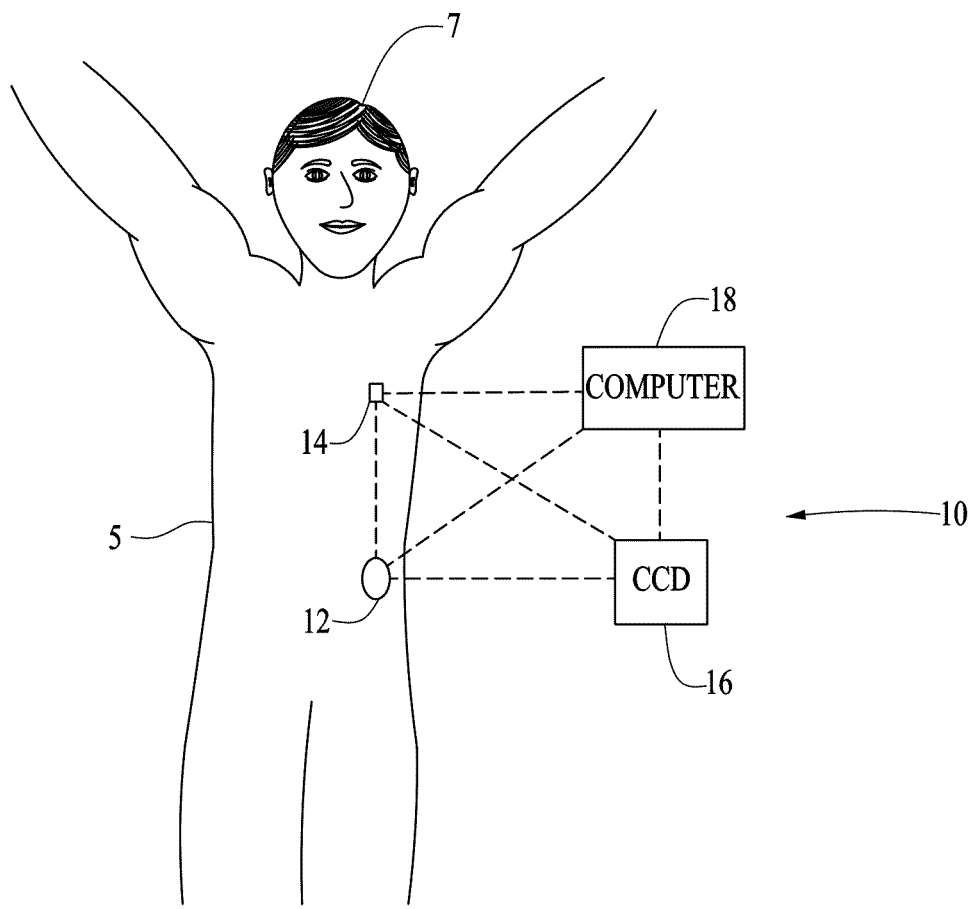
FIG. 1 illustrates a generalized representation of a system in accordance with an embodiment of the present invention.

FIG. 1 illustrates a generalized representation of a monitoring and/or treatment system 10 in accordance with an embodiment of the present invention. The system 10 may allow for providing a treatment regime and/or monitoring physiological parameters of a patient or a user-patient 7. For example, in some embodiments, the system 10 may be providing a treatment regime for diabetes or the like and may monitor blood glucose levels or the like of the user-patient 7. However, in other embodiments, the system 10 need not be limited to a treatment regime for diabetes and/or monitoring blood glucose levels.

The system 10 may include a delivery device 12. The system 10 may further include a sensing device 14, a command control device (CCD) 16, and a computer 18. In various embodiments, the delivery device 12 and the sensing device 14 may be secured at desired locations on a body 5 of the user-patient 7. The locations at which the delivery device 12 and the sensing device 14 are secured to the body 5 of the user-patient 7 in FIG. 1 are provided only as representative, non-limiting, examples.

The system 10, the delivery device 12, the sensing device 14, the CCD 16, and computer 18 may be similar to those described in the following U.S. patent applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S.

patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, Or The Like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional Application Ser. No. 61/044,269, filed Apr. 11, 2008, "Reservoir Plunger Head Systems And Methods"; (xxxvii) U.S. Patent Application Ser. No. 61/044,292, filed Apr. 11, 2008, "Reservoir Barrier Layer Systems And Methods"; (xxxviii) U.S. Patent Provisional Application Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; and (liii) U.S. patent application Ser. No. 12/360,813, filed Jan. 27, 2009, "Multi-Position Infusion Set Device And Process.". In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient 7, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient 7 is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient 7 to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient 7 without the use of, or necessity of, a wire or cable connection between the delivery device 12 and the sensing device 14 and/or the CCD 16.

In some embodiments, the CCD 16 may be for providing information to the user-patient 7 that facilitates a subsequent use of a drug delivery system. For example, the CCD 16 may provide information to the user-patient 7 to allow the user-patient 7 to determine the rate or dose of medication to be administered into the body of the user-patient 7. In other embodiments, the CCD 16 may provide information to the delivery device 12 to control the rate or dose of medication administered into the body of the user-patient 7.

Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

FIGS. 2-6 illustrate various electronic devices, such as a CCD (e.g., CCD 101), which may be employed as an embodiment of the CCD 16 (e.g., FIG. 1) discussed above in accordance with an embodiment of the present invention. In other embodiments, the electronic devices illustrated in FIGS. 2-6 may be any monitoring device, sensing device (e.g., 14 in FIG. 1), and/or any device that may require or otherwise benefit from parameter (e.g., temperature) monitoring and/or compensation as discussed throughout the disclosure.

Although the CCD of FIGS. 2-6 may be similar or used with the embodiments of FIG. 1, it should be understood that the CCD of FIGS. 2-6 may also include some or all of the same components and operate in a manner similar to that shown and described in the embodiments of FIGS. 7-16. In addition, some or all of the features shown in FIGS. 1 and 7-16 may be combined in various ways and included in the embodiments shown in FIGS. 2-6. Likewise, it should be understood that any of the features of the embodiments of FIGS. 2-6 may be combined or otherwise incorporated into any of the other embodiments of FIGS. 2-6 as well as any other embodiment herein discussed.

Figure 2:
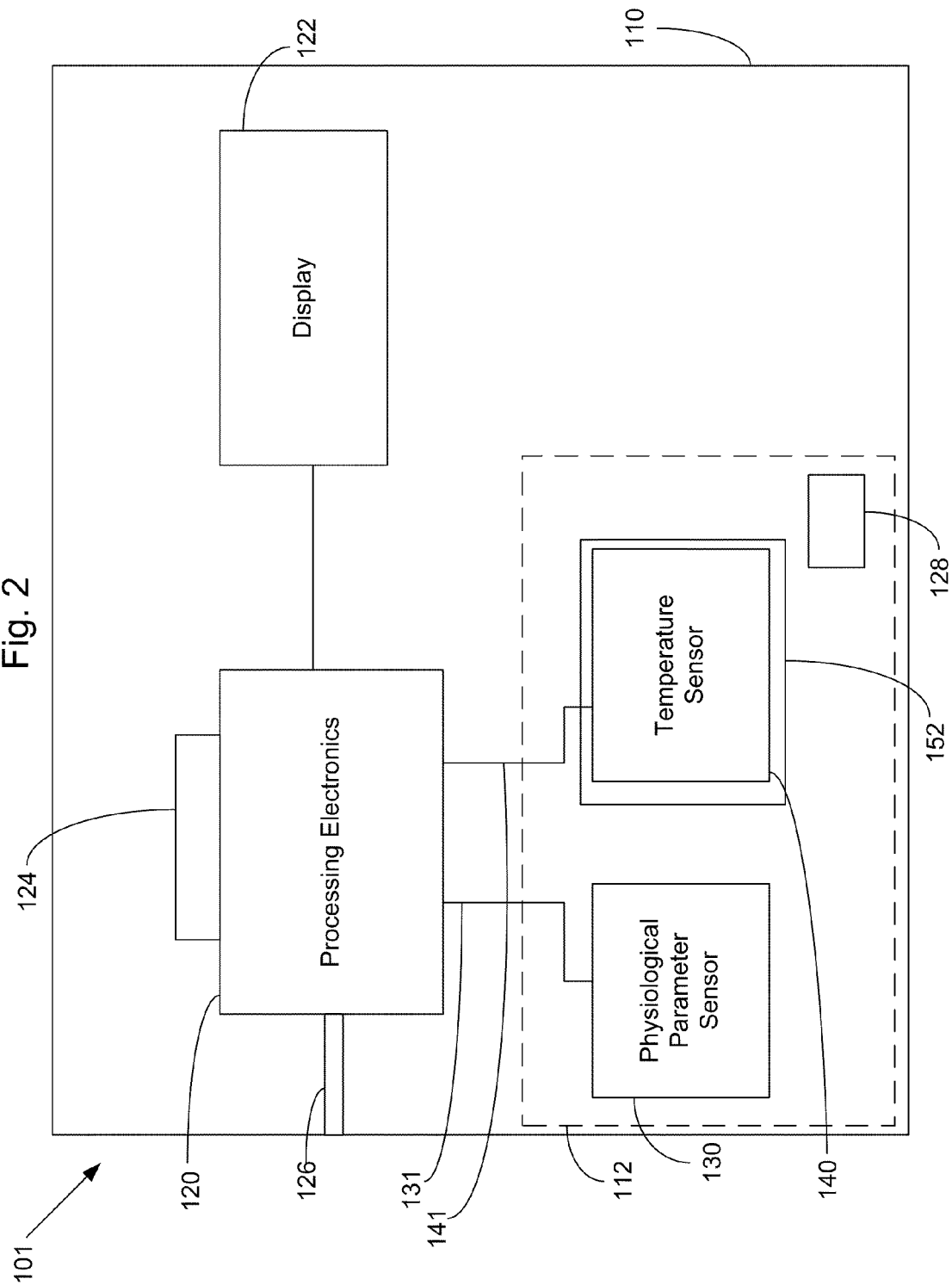
FIG. 2 illustrates a block diagram of a monitoring device in accordance with an embodiment of the present invention.

FIG. 2 is a block diagram of a CCD 101, in accordance with an embodiment of the present invention. The CCD 101 may include, but is not limited to, a housing 110, a processor 120, a first sensor 130, and a second sensor 140. The housing 110 may be made of any suitably rigid material including, but not limited to, plastic, metal, ceramic, glass, composite material, or the like.

The first sensor 130 may be for detecting, sensing, or otherwise measuring a sensed amount of a physiological parameter, such as, but not limited to, blood glucose, oxygen, lactate, and/or the like. The first sensor 130 may be for generating a first signal based on the sensed amount of the physiological parameter. The first sensor 130 may have a response that is partially affected by temperature, pressure, or the like. The first signal may be communicated to the processor 120, which may be configured to interpret this signal to determine an overall amount of the physiological parameter. For example, the first signal may be transmitted from the first sensor 130 to the processor 120 by electrical wiring 131, wireless connection (e.g., RF communication, Bluetooth, etc.), infrared, inductive coupling, and the like.

In some embodiments, the first sensor 130 may be connected to the CCD 101 to transmit the first signal, which may be based upon the measured physiological parameter (e.g., blood glucose, oxygen, lactate, etc.). Accordingly, the CCD 101, or in some embodiments, the processor 120, may utilize the first signal to determine the overall amount of the physiological parameter (e.g., a blood glucose level, an oxygen level, a lactate level, and/or the like).

In some embodiments, the first sensor 130 may be an electrode-type sensor. However, in alternative embodiments, the first sensor 130 may be any one or combination of other types of sensors, such as, but not limited to, electrically-based sensors, chemically-based sensors, optically-based sensors, or the like.

In some embodiments, the first sensor 130 may be located within the housing 110 of the CCD 101. In other embodiments, the first sensor may be located on the housing 110 of the CCD 101, for example, attached to a portion of the housing 110. In yet further embodiments, the first sensor 130 may be separate and spaced apart from the CCD 101. In such embodiments, the first sensor 130 may be electrically connected to the CCD 101, for example by wiring, wirelessly (e.g., RF communication, Bluetooth, etc.), infrared, inductive coupling, and the like.

The second sensor 140 may be a temperature sensor for measuring a temperature. For example, the second sensor 140 may be adapted to measure a temperature at or approximately near a location where the first sensor 130 measures the sensed amount of the physiological parameter. The second sensor 140 may be configured to provide a second signal based on the measured temperature. In other embodiments, the second sensor 140 may be configured to measure one or more parameters, in addition to or alternative to temperature. Such parameters may include, but are not limited to, pressure, force, light intensity, and/or the like.

The second signal may be communicated, for example, to the processor 120, which may be configured to interpret the second signal in combination with the first signal provided by the first sensor 130 to determine the overall amount of the physiological parameter. For example, the second signal may be transmitted from the second sensor 140 to the processor 120 by electrical wiring 141, wireless connection (e.g., RF communication, Bluetooth, etc.), infrared, inductive coupling, and the like. In some embodiments, at least one of the wiring 131, 141 may be made of an electrically conductive material, but with a relatively low thermal conductance.

Measuring the temperature can be used, for example, to calibrate the first sensor 130 or otherwise improve an accuracy of the first sensor 130. For example, for a glucose sensor, the enzyme reaction activity may have a known temperature coefficient. The relationship between temperature and enzyme activity can be used to adjust the sensor values to reflect the actual physiological parameter levels at a given temperature more accurately. Thus, by measuring a temperature at or approximately near a location where the enzyme reaction occurs, the accuracy of the actual physiological parameter levels may be increased.

In some embodiments, the CCD 101 may be configured to provide additional functions that may aid in a treatment regime to which the overall amount of the physiological parameter applies. The CCD 101 may track or otherwise monitor, for example, meals, exercise, and other activities that may affect the treatment regime. These additional functions can be combined with or provided independent from the function of determining a physiological parameter determined by the CCD 101.

The CCD 101 may include other components to support and/or complement the processor 120 in performing functions. The CCD 101 may include electronic memory (not shown) for storing data and instructions used by the processor 120. The CCD 101 may include a data entry device (not shown), such as a keypad, or the like, for receiving a direct input from the user-patient.

In some embodiments, the CCD 101 may also include a display 122, such as a liquid crystal display (LCD), LED, or the like, for providing information, or the like, to the user-patient. The display 122 may be color, for example, and may produce a significant amount of heat within the housing 110 of the CCD 101. Other components within the CCD 101 may also produce a significant amount of heat. Because accuracy of a reading of an amount of a physiological parameter, for example as measured by the first sensor 130, is dependent on temperature, the accuracy of the parameter reading may be reduced by the significant amount of heat. Accordingly, in some embodiments, the second sensor 140, which may be a temperature sensor, may be located, configured, or otherwise adapted to be thermally insulated such that a temperature measured by the second sensor 140 may be approximate to an ambient temperature where a reaction of the first sensor 130 (i.e., where physiological parameter measured) occurs.

Thus, in various embodiments, by using a measured temperature that is approximate a temperature where a physiological parameter is measured, accuracy of the measurement of the physiological parameter may be increased.

In some embodiments, the CCD 101 may include a data port (not shown), such as a digital input/output (I/O) port, or the like. In such embodiments, the data port may allow the CCD 101 to communicate with a computer (not shown). To facilitate communication, the CCD 101 may interface with the computer through a communication station (not shown) that may serve as a docking station for the CCD 101, for example.

In some embodiments, the data port within the CCD 101 may be directly connectable to the computer. Through the data port, data may be downloaded from the CCD 101, such as stored physiological parameter readings, settings, programs, and other information related to functions of the CCD 101. Thus in some embodiments, advanced analysis can be performed on the computer, freeing memory (not shown) within the CCD 101. Data such as physiological parameter readings, settings, and programs may also be downloaded to the CCD 101. In this way, the CCD 101 may be conveniently reprogrammed without requiring tedious manual entry by the user-patient.

In some embodiments, the CCD 101 may be configured to receive information, such as glucose data or the like, from the first sensor 130 and may display and/or log the received information. For example, logged data can be downloaded from the CCD 101 to a PC, laptop, or the like, for detailed data analysis. In further embodiments, the CCD 101 may be used in a hospital environment, or the like. In yet further embodiments, the CCD 101 may include one or more buttons to record data and events for later analysis, correlation, or the like. Further buttons may include a sensor on/off button to conserve power and to assist in initializing the first sensor 130.

In some embodiments, the CCD 101 may be configured to provide sensing and advanced predictive functions, which may be designed, for example, to anticipate unsafe conditions for the user-patient before they occur. In addition, predictive functions can be employed so that the user-patient can obtain feedback to obtain a desired physical objective, such as maximizing athletic performance. Other functions of the monitor may include, but is not limited to, multiple programmable alarms, reminders, diagnostic functions, and the like. Advanced alarm functions may include an alarm repeat delay function and a snooze function that can be set by the user-patient.

In some embodiments, the CCD 101 may include advanced display tools to facilitate easy and quick interpretation of information related to the user-patient's condition, including, but not limited to, a display function for an alarm history as well as a history of measurements, and the like. In some embodiments, the alarm functions may be configured to provide a warning to the user-patient in a case where a threshold of the physiological parameter or other parameter (e.g., temperature) is surpassed. For example, the CCD 101 may provide such a warning in a case where the physiological parameter is too high or too low. The warning may be any indicator that can be perceived by the user-patient, for example an audio sound, a visual indicator (e.g., a blinking light), and/or a vibration, or the like. For example, a user-patient may be notified if the ambient temperature, for example as measured by the second sensor 140, is sufficiently high to cause damage to the device, affect the insulin or other drug to be delivered to the user-patient, harm the user-patient, and/or the like In some embodiments, the housing 110 of the CCD 101 may be adapted to contain at least one of the processor 120, the first sensor 130, and the second sensor 140. In other embodiments, the housing 110 need not include any of the processor 120, the first sensor 130, and the second sensor 140. In such embodiments, the processor 120, the first sensor 130, and the second sensor 140 may be configured or adapted to communicate with the CCD 101, for example, wirelessly, or the like.

Figure 3B:
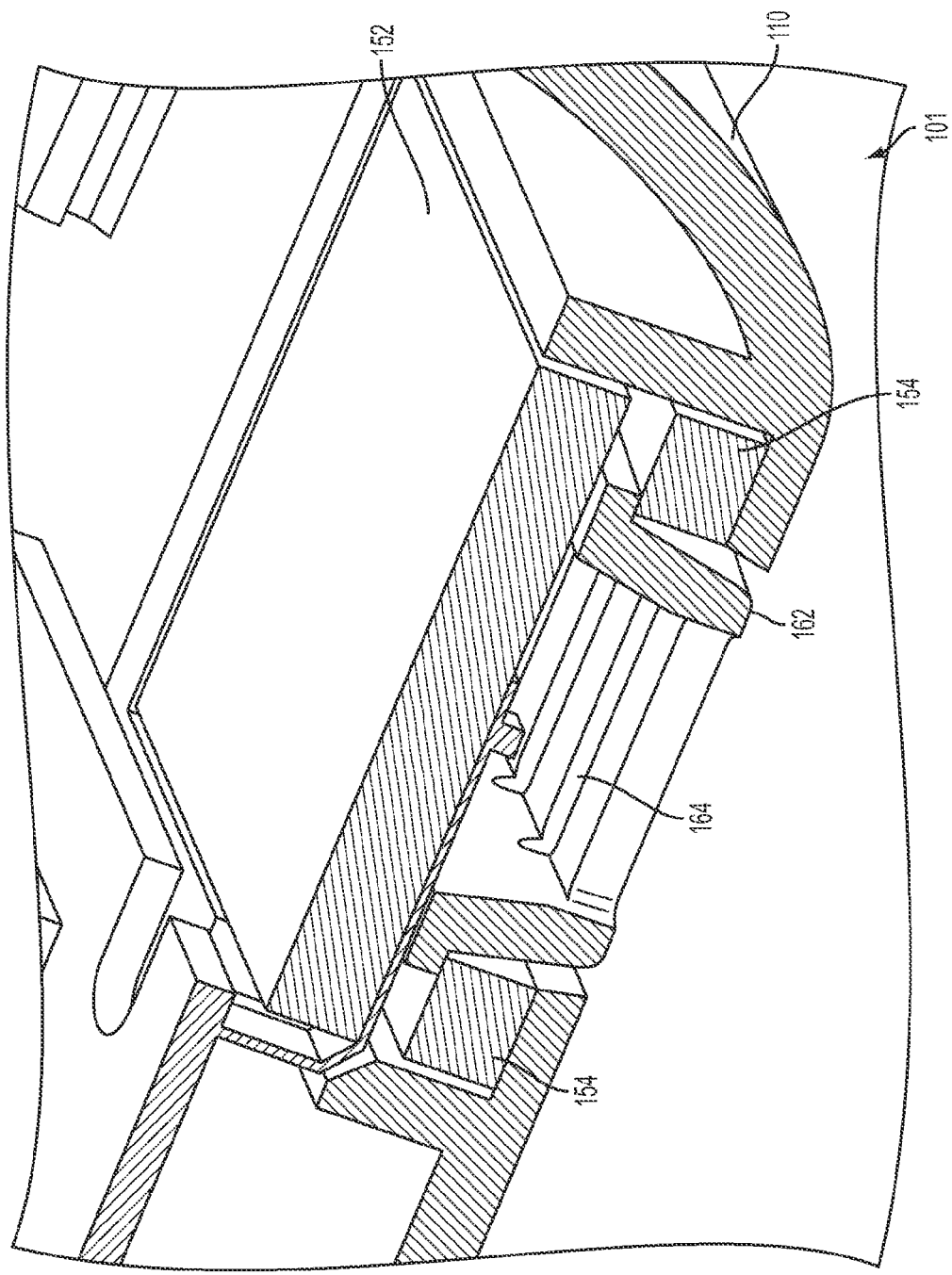

In some embodiments, such as the embodiments exemplified in FIGS. 2, 3A, and 3B, the housing 110 of the CCD 101 may include a chamber 112. The second sensor 140 may be disposed in the chamber 112, or otherwise isolated from electronics (e.g., the processor 120 and the display 122 in FIG. 6) in or on the housing 110. In some embodiments, the second sensor 140 may be exposed to ambient air (e.g., air outside the housing 110 of the CCD 101). For example, the housing 110 may include one or more openings, grooves, or vents (not shown) that may extend through a portion of the housing 110 to expose the second sensor 140 to ambient air. Accordingly, this may allow the second sensor 140 to measure a temperature that is approximate to an ambient temperature.

In other embodiments, the housing 110 may include a cover (not shown) for at least partially covering the chamber 112. The cover may include one or more openings, grooves, or vents that may extend through a portion of the cover to expose the second sensor 140 to ambient air. The cover may be made of any suitably rigid material including, but not limited to, plastic, metal, ceramic, glass, composite material, or the like. In some embodiments, the housing 110 may include vents (not shown) to provide expose at least a portion of the housing 110, such as the processor 120, the display device 122, the chamber 112, and/or the second sensor 140 to ambient air.

In some embodiments, the housing 110 may include a first thermal insulation material 152 configured to insulate at least partially the second sensor 140 and/or the chamber 112 from heat generated by electronics (e.g., the processor 120 and/or the display 122 in FIG. 6) inside the housing 110 external to the chamber 112. The first thermal insulation material 152 may cover or surround at least a portion of the second sensor 140 and/or the chamber 112 to mitigate heat generated by the electronics from affecting a measurement by the second sensor 140.

In further embodiments, the housing 110 may include a second thermal insulation material 154 configured to insulate at least partially the second sensor 140 and/or the chamber 112 from heat generated by the electronics inside the housing 110 external to the chamber 112. The second thermal insulation material 154 may cover or surround at least a portion of the second sensor 140 and/or the chamber 112 to mitigate heat generated by the electronics from affecting a measurement by the second sensor 140. In some embodiments, the first thermal insulation material 152 may be a same material as the second thermal insulation material 154. In other embodiments, the first thermal insulation material 152 may be a different material from the second thermal insulation material 154.

In other embodiments, the housing 110 may include a cradle or tray-like support structure 162 configured, shaped, or otherwise adapted for placement in the chamber 112. For example, the support structure 162 may allow the second sensor 140 to be placed in the chamber 112 without contacting or otherwise reducing surface area in contact with the housing 110. The support structure 162 may be integrated with the housing 110 or may be removable. For example, the support structure may be removably attachable to the housing 110. A tab 114, flange, or the like may extend from the housing 110 into at least a portion of the chamber 112 for supporting or otherwise holding the support structure 162 within the chamber 112.

The support structure 162 may be made of any suitably rigid material including, but not limited to, plastic, metal, ceramic, glass, composite material, or the like. The support structure 162 may be configured, shaped, or otherwise adapted to receive and support the second sensor 140. In further embodiments, the support structure 162 may include a plurality of openings, grooves, or vents 164. The vents 164, for example, may extend through a portion of the support structure to expose the second sensor 140 to ambient air (e.g., air outside the housing 110 of the CCD 101). Accordingly, this may allow the second sensor 140 to measure a temperature that is approximate to an ambient air temperature.

In some embodiments, the first thermal insulation material 152 may cover or surround at least a portion of the support structure 162 and/or the second sensor 140 to mitigate heat generated by the electronics from affecting a measurement by the second sensor 140. For example, the first thermal insulation material 152 may be disposed over the support structure 162 and/or the second sensor 140. In some embodiments, the second thermal insulation material 154 may cover or surround at least a portion of the support structure 162 and/or the second sensor 140 to mitigate heat generated by the electronics from affecting a measurement by the second sensor 140. For example, the second thermal insulation material 154 may be adapted to surround at least a portion of the support structure 162.

In various embodiments, the housing 110 may include one or more temperature control devices 128. In some embodiments, the temperature control device 128 may be a temperature-dissipating device, such as a heat sink, and/or the like. The heat sink may be made of temperature dissipating material (e.g., copper and/or the like) adapted to dissipate heat away from at least a portion of the housing 110, such as the processor 120, the display device 122, the chamber 112, and/or the second sensor 140. The heat sink may be positioned at any suitable location within or on the housing 110 to dissipate heat within or otherwise away from the housing 110.

For example, the heat sink may be attached to the second sensor 140, a structure within the chamber 112, any of the electronics (e.g., processor 120, display 122) within the housing 110, or the like.

In some embodiments, the heat sink may be a block of machined metal that may be attached to the part that needs cooling (e.g., the second sensor 140, the processor 120, the display device 122, or the like). An adhesive may be used, or a clamp may be used to affix the heat sink on or over the part with a thermally conductive pad or gel spread in between the heat sink and the part. The heat sink may have fins and ridges to increase a surface area of the heat sink for increased heat dissipation capabilities. In some embodiments, a heat conductivity of the metal of the heat sink may be better than that of air. In particular embodiments, the ability of the metal of the heat sink to radiate heat may be better than that of the component the heat sink is protecting. For example, the heat sink may be made of aluminum, copper, or the like.

In further embodiments, the housing 110 may include a fan (not shown) adapted to direct air (e.g., ambient temperature air, or cooled air) onto the heat sink to allow the heat sink to dissipate more heat than embodiments in which, for example, a fan is not provided with the heat sink. In other embodiments, the fan (not shown) may be adapted to direct heated air away from the heat sink to allow the heat sink to dissipate more heat than embodiments in which, for example, a fan is not provided with the heat sink. These embodiments may result in more air being blown through the heat sink, increasing a rate at which the heat sink can exchange heat with the ambient air.

In some embodiments, the temperature control device 128 may be a thermally conducting device, such as a "heat antenna" and/or the like, that may be adapted to transfer or otherwise convey an ambient temperature to at least a portion of the housing 110, such as the processor 120, the display device 122, the chamber 112, and/or the second sensor 140. The heat antenna may be made of a thermally conductive material (e.g., copper). The heat antenna may be positioned at any suitable location for conveying an ambient temperature, for example, to the component being protected by the heat antenna. The heat antenna may be configured in any manner known in the art that may facilitate the conveying of ambient temperature to the component. For example, the heat antenna 126 may be adapted to extend from outside the housing 110 of the CCD 101 to the processor 120, the second sensor 140, and/or the like.

In some embodiments, the temperature control device 128 may be a ventilation device, such as a fan, and/or the like, adapted to dissipate heat away (e.g., heated air) from at least a portion of the housing 110, such as the processor 120, the display device 122, the chamber 112, and/or the second sensor 140. The fan may be positioned at any suitable location within or on the housing 110 to dissipate heat within the housing 110. For example, the fan may be located in the chamber 112 and/or the fan may be attached to the second sensor 140, any of the electronics (e.g., processor 120, display 122) within the housing 110, or the like. Thus in various embodiments, one or more suitable temperature control devices and/or techniques may be employed to dissipate heat from within the housing 110 and/or pull in ambient air into the device (and/or a particular component thereof).

In other embodiments, the fan may be adapted to direct air (e.g., ambient temperature air, or cooled air) into at least a portion of the housing 110, such as onto the processor 120, the display device 122, the second sensor 140, and/or into the chamber 112. Such embodiments may reduce a temperature of the portion of the housing 110. In addition, such embodiments (and/or other embodiments using other temperature control devices) may increase a temperature of a portion of the housing 110 that may be otherwise below optimal operating conditions. For instance, if the CCD 101 is left in a sufficiently cool environment for long enough, portions of the CCD 101, for example, where the first sensor 130 is located may be at lower temperature than the location at which a temperature is measured by the second sensor 140. Thus in various embodiments, a fan (and/or other temperature control device) may be employed to raise or otherwise equalize the temperature where the first sensor 130 is located to that of the location measured by the second sensor 140.

In various embodiments, the housing 110 may include at least one of any suitable temperature control device and/or employ at least one of any suitable techniques to reduce a temperature of at least a portion of the housing 110, such as, but not limited to, an air-cooling device, forced-cooling device, a liquid submersion cooling device (e.g., submersion of components in a thermally conductive liquid), a Peltier device, conductive and radiative cooling (e.g., components in contact with the housing 110 to increase surface area to radiate and exchange more heat), water cooling device, a heat pipe containing a heat transfer liquid, phase-change cooling, liquid nitrogen, soft cooling (e.g., program software configured to minimize energy use of the CCD 101 or components thereof), undervolting (e.g., running the CCD 101 or components thereof at a voltage below specifications), or the like.

In some embodiments, the chamber 112 may be strategically located within the housing 110 separated from and arranged as far as practical from electronics of the CCD 101, such as the processor 120, the display 122, or the like. In some embodiments, the chamber 112 may be strategically located within the housing 110 at a location minimally affected by temperature changes produced by the electronics, such as the processor 120, the display 122, or the like. It should be noted that, in other embodiments, the chamber 112 need not be located at a location furthest from the electronics or at a location minimally affected by temperature changes produced by the electronics. In such embodiments, the chamber 112 may be located sufficiently away from the electronics to minimize an effect from the heat-generating electronics in the CCD 101 on temperature(s) near the first sensor 130 and/or the second sensor 140.

In some embodiments, the first sensor 130 may be disposed within the chamber 112 along with the second sensor 140 at any suitable location relative to the CCD 101. The housing 110 may be configured or adapted to allow the first sensor 130 to receive a sample of a material associated with the physiological parameter measurable by the first sensor 130. For example, in some embodiments, the housing 110 may include an opening in communication with the first sensor 130 to receive a sample of the material. In some embodiments, a portion of the first sensor 130 may extend to or beyond an external surface of the housing 110 to receive a sample of the material.

Figure 5:
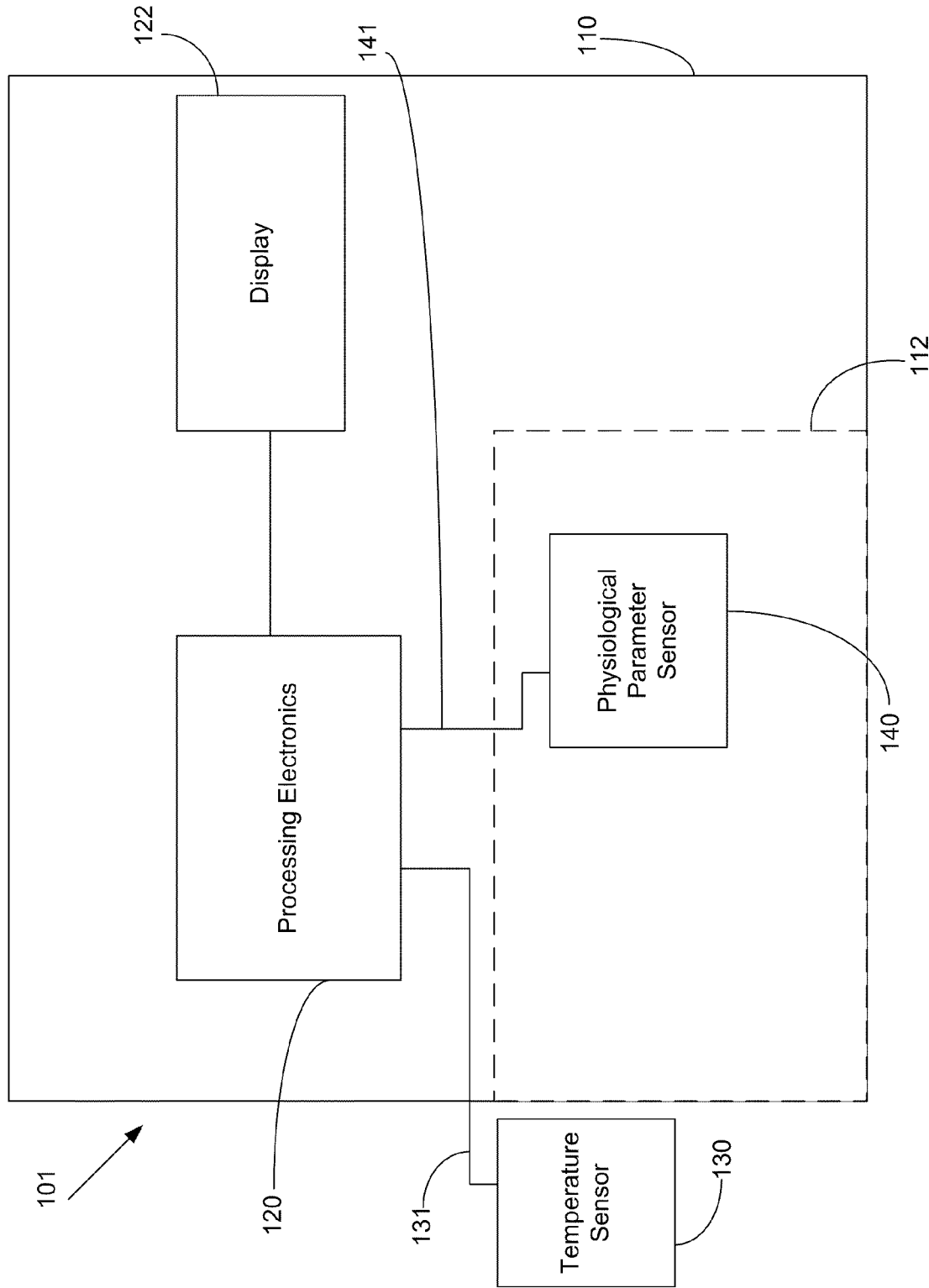
FIG. 5 illustrates a block diagram of a monitoring device in accordance with an embodiment of the present invention.

In some embodiments, the first sensor 130 may be located within the chamber 112. The second sensor 140 may be located outside of the chamber, for example external to the housing 110, as shown in FIG. 5. Alternatively, the first sensor 130 may be located, but not limited to, outside the chamber 112 (e.g., FIG. 4), separate from the housing 110 (e.g., FIG. 4), on an external surface of the housing 110, inside the housing 112, or the like.

In various embodiments, the second sensor 140 may be disposed within the housing 110 without a need for an isolated chamber 112 as previously described. In such embodiments, the second sensor 140 may be configured or adapted to be used with any one or combination of the temperature control devices and techniques described above (e.g., a first thermal insulation material, a second thermal insulation material, vents, a fan, a heat sink, and/or the like). Moreover, in some embodiments, the second sensor 140 may be strategically located within the housing 110 at a location sufficiently or maximally separated or otherwise sufficiently insulated from the electronics, such as the processor 120, the display 122, or the like for thermal insulation.

In some embodiments, the second sensor 140 may be strategically located within the housing 110 at a location minimally affected by temperature changes produced by the electronics, such as the processor 120, the display 122, and/or the like. It should be noted that, in other embodiments, the second sensor 140 need not be located at a location furthest from the electronics or at a location minimally affected by temperature changes produced by the electronics. In such embodiments, the second sensor 140 may be located sufficiently away from the electronics to minimize an effect from the heat-generating electronics in the CCD 101 on temperature(s) near the first sensor 130 and/or the second sensor 140.

Figure 6:
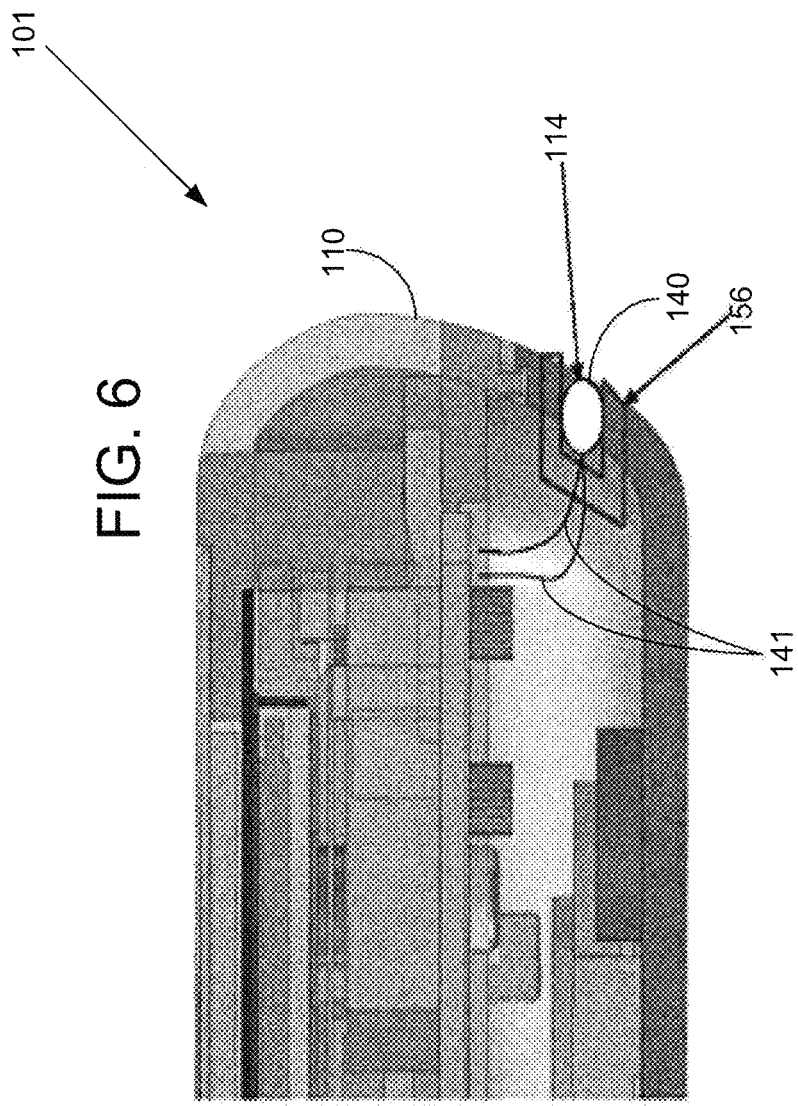
FIG. 6 illustrates a monitoring device in accordance with an embodiment of the present invention.

In some embodiments, such as the embodiment exemplified in FIG. 6, the second sensor 140 may be located at least partially within the housing 110, but at a location such that the second sensor 140 is at least partially directly exposed to ambient air temperature. For example, a first portion of the second sensor 140 may be exposed to air outside the housing 110 through a hole 114 or vents. In further embodiments, a second portion of the second sensor 140 may be covered or surrounded by a thermal insulation material 156. The insulation material 156 may be for thermally insulating the second sensor 140 from heat provided by a temperature source within the CCD 101, such as the processor (not shown), display (not shown), or the like. The thermal insulation material 156 may be like the first insulation material 152 and/or the second insulation material 154. In other embodiments, the thermal insulation material 156 may different from the first insulation material 152 and the second insulation material 154.

Figure 16:
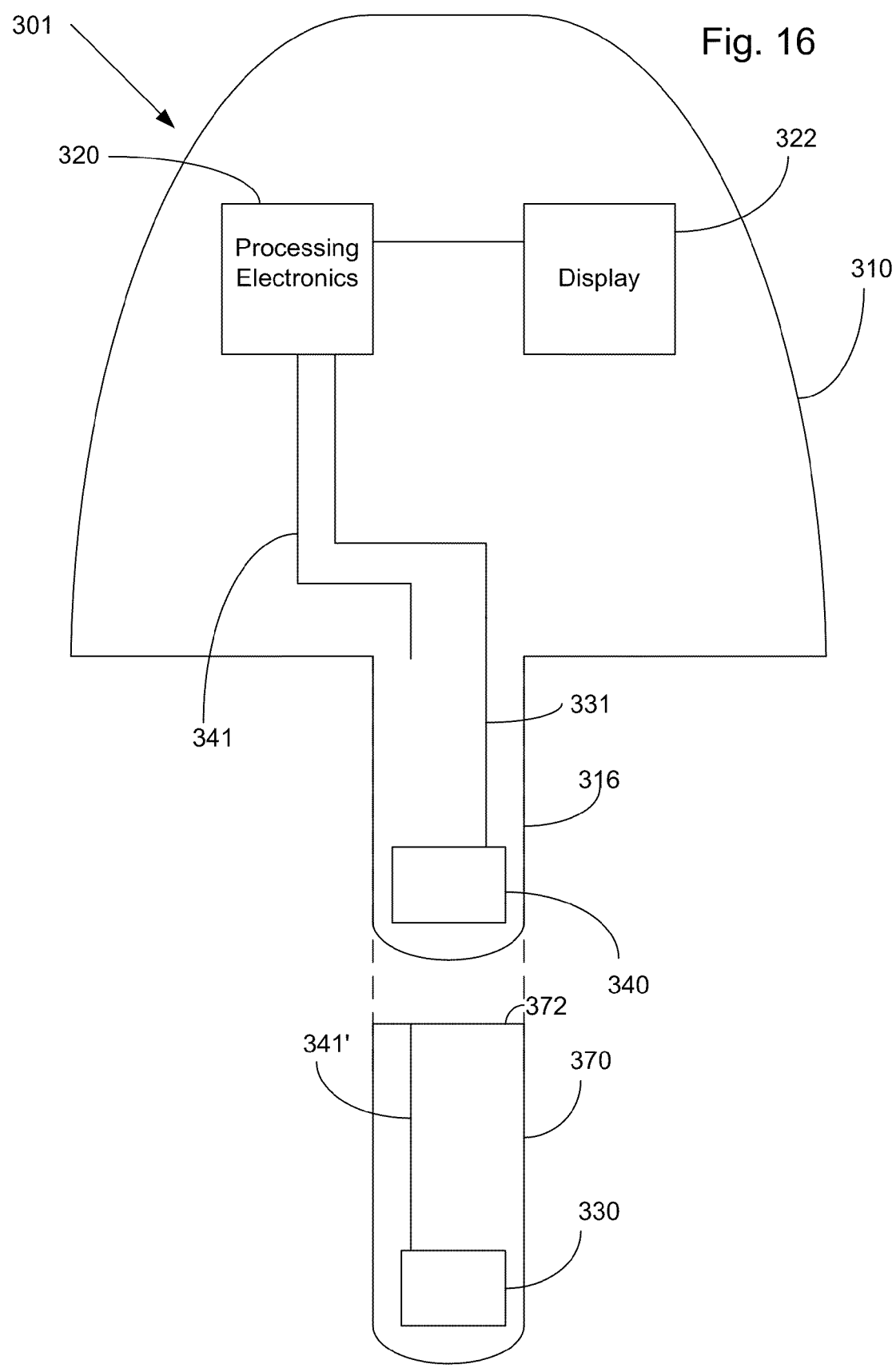
FIG. 16 illustrates a block diagram of a monitoring device in accordance with an embodiment of the present invention.

Returning to FIGS. 2-6, in some embodiments, the housing 110 of the CCD 101 may include a portion extending away from the housing 110, such as a tab (e.g., 16 in FIG. 16). At least one of the first sensor 130 and the second sensor 140 may be located in or on the tab at a location further spaced apart from heat-generating electronics in the CCD 101. In such embodiments, location(s) of the first sensor 130 and/or the second sensor 140 may be sufficiently spaced away and/or otherwise sufficiently insulated from the heat-generating electronics within the CCD 101 to minimize an effect from the heat-generating electronics in the CCD 101 on temperature(s) near the first sensor 130 and/or the second sensor 140. In further embodiments, the tab may include a chamber that functions as previously described with respect to the chamber 112.

In other embodiments the first sensor 130 may be located in or on a first tab (not shown) and the second sensor 140 may be located in or on a second tab (not shown). In some embodiments, the first tab may have a size and/or a shape similar to a size and/or a shape of the second tab.

In some embodiments, the first tab and the second tab may be located relative to one another such that the second sensor 140 may be at least partially in alignment (e.g., vertical alignment or horizontal alignment) with the first sensor 130. Accordingly, in such embodiments, the first sensor 130 and the second sensor 140 may be close to each other or in contact with each other. This may allow the second sensor 140 to measure a temperature at a location that is approximate to a location of the first sensor 130. Furthermore, in such embodiments, the locations of the first sensor 130 and the second sensor 140 may be located sufficiently spaced away and/or otherwise sufficiently insulated from heat produced by electronics within the CCD 101 to minimize an effect of such heat on temperature(s) near the first sensor 130 and/or the second sensor 140.

In various embodiments, the CCD 101 may include a third sensor (not shown) and/or additional sensors. In some embodiments, the third sensor may be a similar type of sensor as the second sensor 140. For instance, in a case where the second sensor 140 is a temperature sensor, the third sensor may be a temperature sensor arranged, for example, to measure a temperature at a different location (e.g., near the processor 122) from the second sensor 140. In further embodiments, the third sensor may be configured to provide a signal based on the measured temperature. The signal may be communicated, for example, to the processor 120 (and/or other sensors), which may be configured to interpret the signal in combination with one or more of the first signal and the second signal provided by the first sensor 130 and the second sensor, respectively to determine, for example, the overall amount of the physiological parameter.

In other embodiments, the third sensor may be a different type of sensor from the second sensor 140. For instance, in a case where the second sensor 140 is a temperature sensor, the third sensor may be a sensor for measuring one or more parameters, in addition to or alternative to temperature. Such parameters may include, but are not limited to, pressure, force, light intensity, and/or the like.

In some embodiments, one or both of the first sensor 130 and the second sensor 140 may be sufficiently located away or otherwise sufficiently insulated from portions of the housing 110 exposed to ambient air (e.g., ambient air temperature) or otherwise affected by ambient air. In some embodiments, the housing 110, portions thereof, and/or components within may be made of a material selected to have a thermal mass for mitigating the effect of temperature of ambient air (e.g., a cold environment or a hot environment) on one or more of the first sensor 130 and the second sensor 140. For example, in a case where the CCD 301 is left in a cool first environment and then moved to a warmer second environment where the physiological parameter is measured by the first sensor 130, the second sensor 140 may better measure a temperature where the measurement of the physiological parameter is performed (e.g., the second environment). Otherwise, the second sensor 140 may measure a temperature closer to the first environment than the second environment thus reducing the accuracy of the physiological parameter measurement by the CCD 101.

FIGS. 7-11 illustrate various electronic devices, such as a CCD (e.g., CCD 201), which may be employed as the CCD 16 (e.g., FIG. 1) or any other device discussed throughout the disclosure in accordance with an embodiment of the present invention. Although the CCD of FIGS. 7-11 may be similar or used with the embodiments of FIGS. 2-6, it should be understood that the CCD of FIGS. 7-11 may also include some or all of the same components and operate in a manner similar to that shown and described in the embodiments of FIGS. 1 and 12A-16. In addition, some or all of the features shown in FIGS. 1-6 and 12A-16 may be combined in various ways and included in the embodiments shown in FIGS. 7-11. Likewise, it should be understood that any of the features of the embodiments of FIGS. 7-11 may be combined or otherwise incorporated into any of the other embodiments of FIGS. 7-11 as well as any other embodiment herein discussed.

Figure 7:
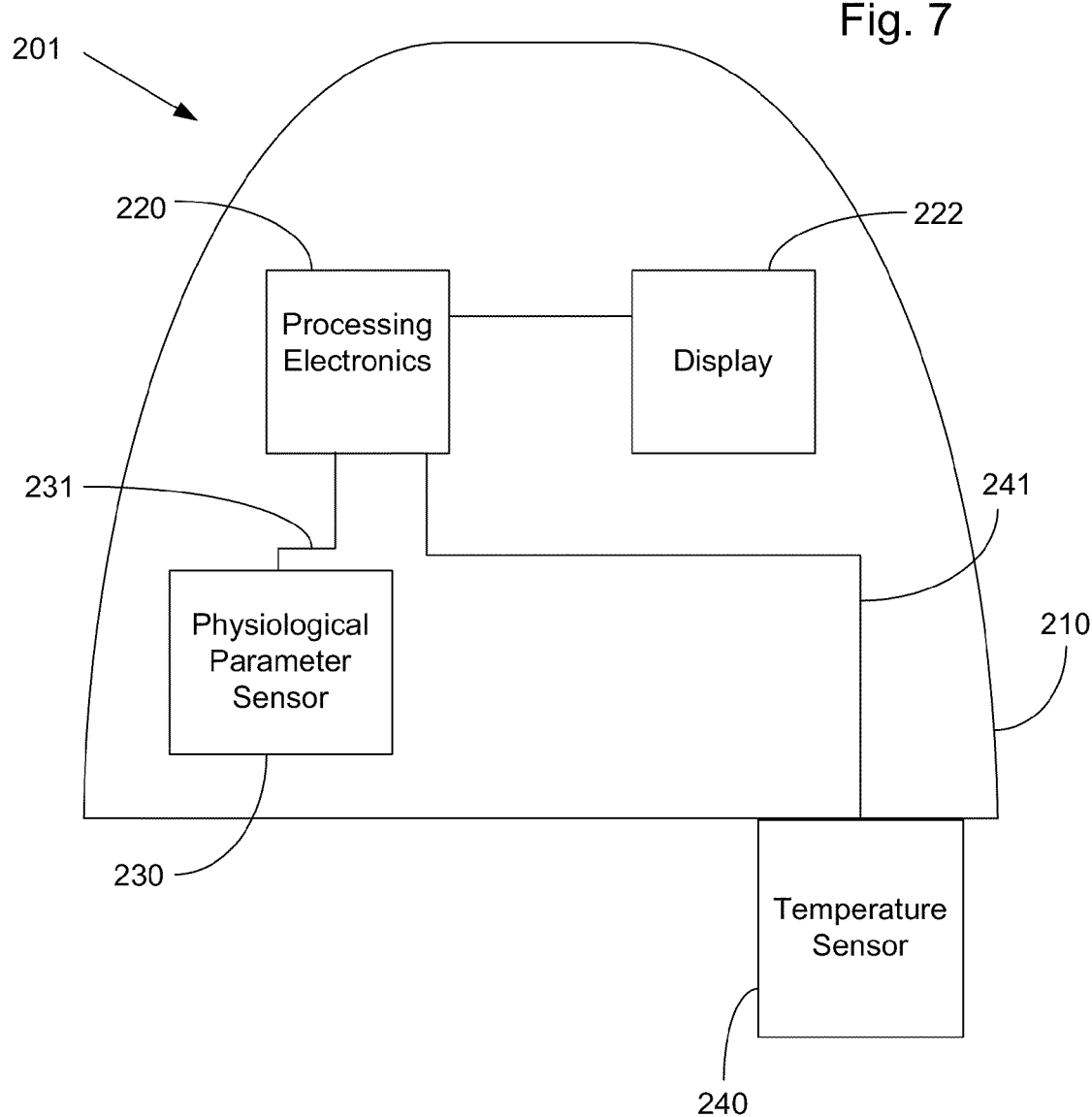
FIG. 7 illustrates a block diagram of a monitoring device in accordance with an embodiment of the present invention.

FIG. 7 illustrates a CCD 201 according to an embodiment of the present invention. The CCD 201 may be similar to the CCD 101 previously discussed. For example, the CCD 201 may include a housing 210, a processor 220, a first sensor 230, and a second sensor 240. In some embodiments, the CCD 201 may further include a display device 222, which may be similar to the display device 122 (e.g., FIGS. 2-6).

In some embodiments, the second sensor 240 may be located at least partially on an external surface of the housing 210 of the CCD 201. In such embodiments, the second sensor 240 may be exposed to air, and thus ambient temperature. The second sensor 240 may be connected with the processor 220 via electrical wiring 241, such as, but not limited to, a flex cable 241. In some embodiments, the electrical wiring 241 connecting the second sensor 240 with the processor 220 may be similar electrical wiring 231 connecting the first sensor 230 and the processor 220. In other embodiments, the electrical wiring 241 connecting the second sensor 240 with the processor 220 may be different from the electrical wiring 231 connecting the first sensor 230 and the processor 220.

Figure 8:
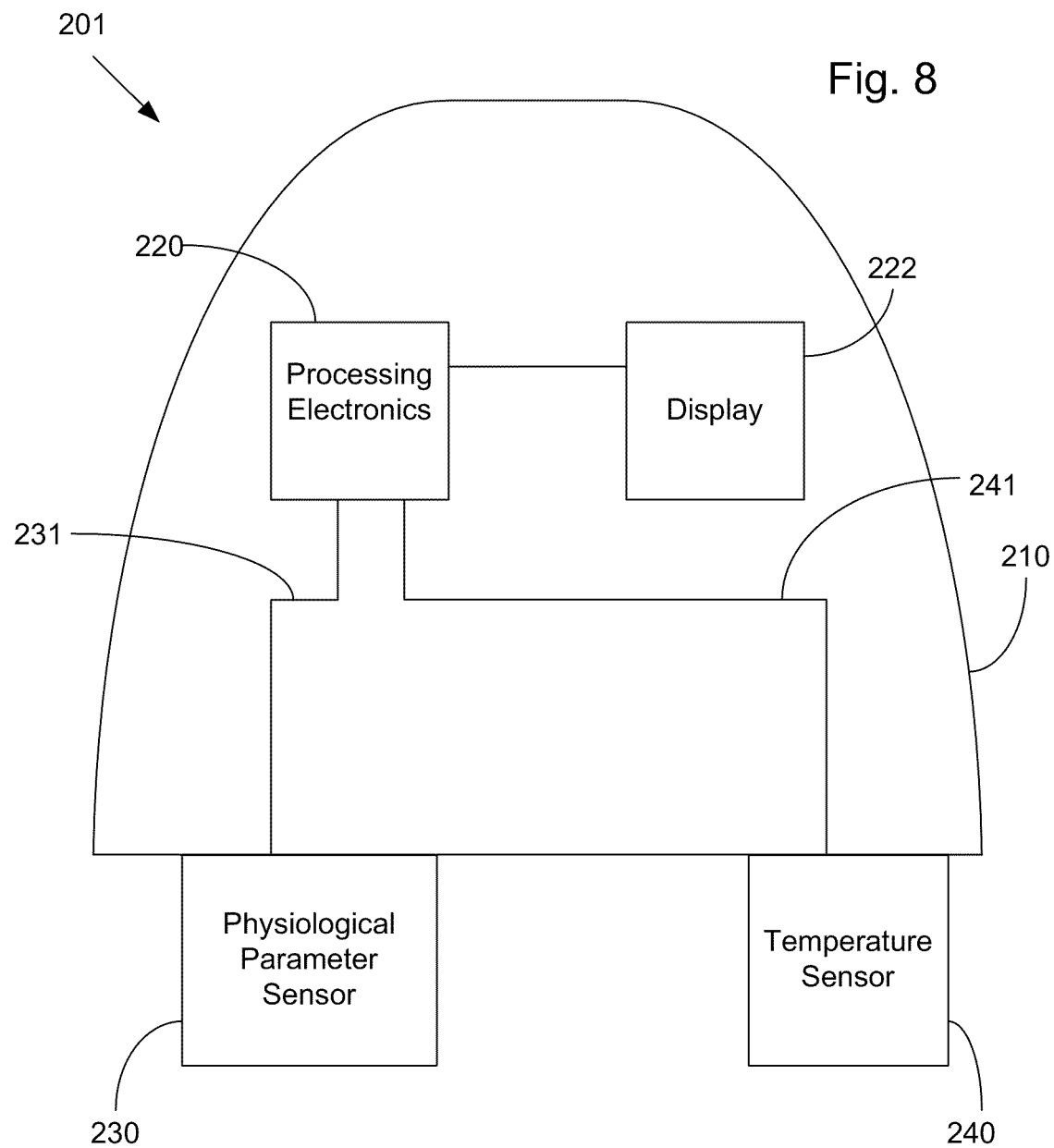
FIG. 8 illustrates a block diagram of a monitoring device in accordance with an embodiment of the present invention.
Figure 9:
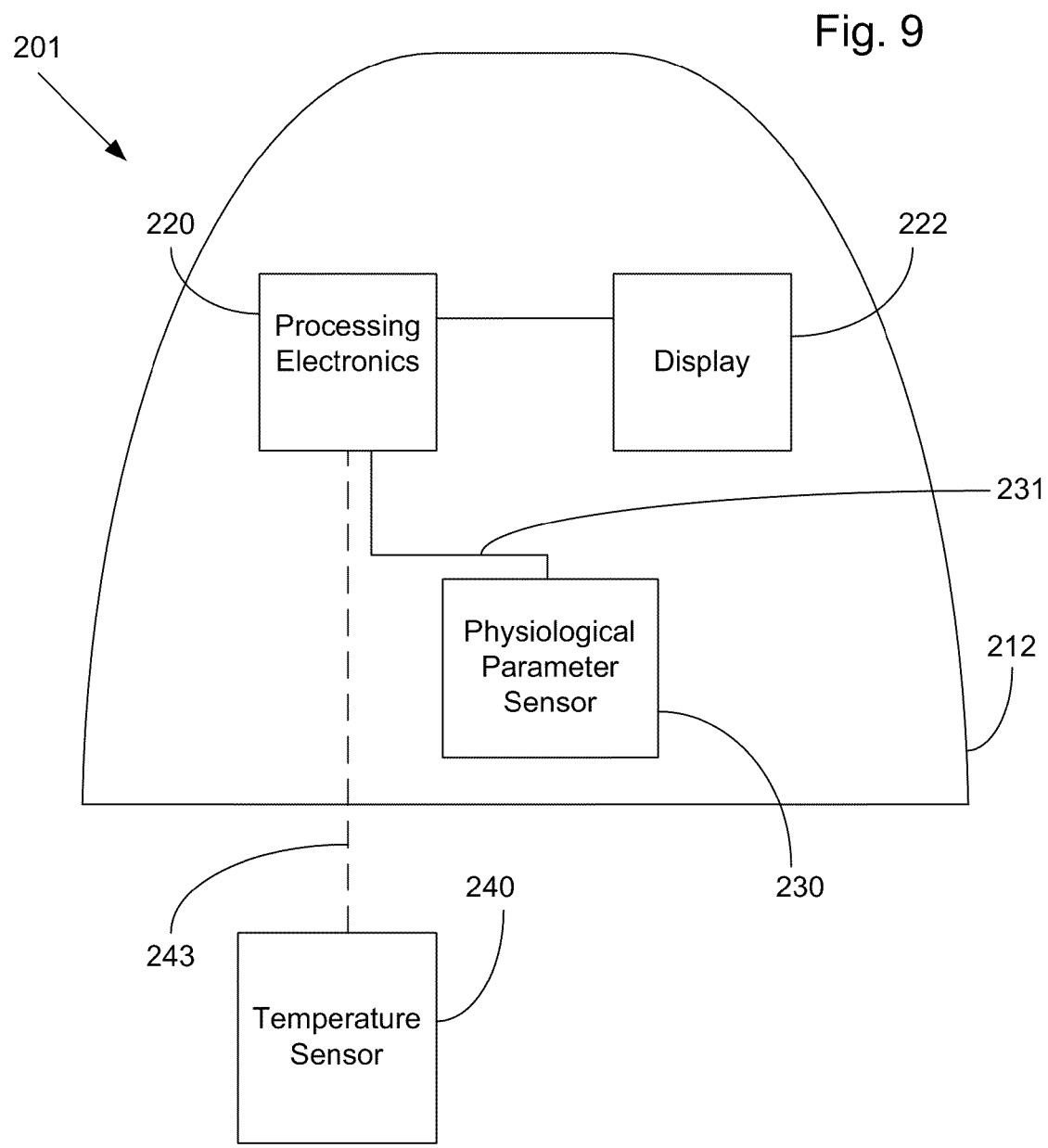
FIG. 9 illustrates a block diagram of a monitoring device in accordance with an embodiment of the present invention.

In some embodiments, such as the embodiment shown in FIG. 8, the first sensor 230 may be located at least partially on an external surface of the housing 210 of the CCD 201, for example (but not limited to) near the second sensor 240. In other embodiments, such as the embodiment shown in FIG. 9, the second sensor 240 may be configured or otherwise adapted to be separate (e.g., spaced apart) from the CCD 201. The second sensor 240 may be configured to communicate wirelessly with the CCD 201 through a wireless communication link 243. For example, the second sensor 240 may include a transmitter (not shown) and/or a receiver (not shown) for communicating with a receiver (not shown) and/or transmitter (not shown) of the CCD 201. In other embodiments, the CCD 201 may include a connector (not shown) for connecting the second sensor 240 with the CCD 201. The connector may be, for example, one or more electrically conductive wires, or the like.

In further embodiments, such as the embodiments shown in FIGS. 10 and 11, the first sensor 230 may be configured or otherwise adapted to be separate (e.g., spaced apart) from the CCD 201. The first sensor 230 may be configured to communicate wirelessly with the CCD 201 through a wireless communication link 233. For example, the first sensor 230 may include a transmitter (not shown) and/or a receiver (not shown) for communicating with a receiver (not shown) and/or transmitter (not shown) of the CCD 201. In other embodiments, the CCD 201 may include a connector (not shown) for connecting the first sensor 230 with the CCD 201. The connector may be, for example, one or more electrically conductive wires, or the like.

In some embodiments, the first sensor 230 may be connected to the second sensor 240 with a connector 235, as exemplified in FIG. 11. The connector 235 may be, for example, one or more electrically conductive wires, a wireless communication link, and/or the like. The first sensor 230 and the second sensor 240 may be tethered or otherwise connected to the CCD 201 via connection 275 or may be configured to communicate wirelessly with the CCD 201, for example, in a manner similar to that described with respect to FIGS. 9 and 10.

Returning to FIG. 11, in some embodiments, the first sensor 230 and the second sensor 240 may be part of a sensing device 270 (or other device including both sensors). The sensing device 270 and/or components thereof (e.g., the first sensor 230 and/or the second sensor 240) may be configured to communicate with the CCD 201, for example though a wireless communication link 275 or through a connector (not shown) for connecting the sensing device 270 and the CCD 201. For example, the sensing device 270 (and/or individual components thereof) may be configured to gather data (e.g., temperature, parameter information) and transmit the data to the CCD 201 for the processor 220 to process the data. In these embodiments, the second sensor 240 may be thermally insulated and/or strategically positioned relative to heat-generating electronics of the sensing device 270 in accordance with any one or combination of manners previously described.

In further embodiments, the sensing device 270 may include a processor (not shown) configured to process some or all of the data before transmitting sensor information to the CCD 201. In these embodiments, the second sensor 240 may be thermally insulated and/or strategically positioned relative to the processor of the sensing device 270 and/or other heat-generating electronics of the sensing device 270 in accordance with any one or combination of manners previously described.

In various embodiments, the first sensor 230 and the second sensor 240 may be located in the same ambient location, for example, on an external surface of the housing 210. In various embodiments, the first sensor 230 may be located in a thermal zone (not shown) having a known temperature. The known temperature of the thermal zone may be measured or otherwise detected by, for example, the second sensor 240 or other sensor. In some embodiments, the known temperature of the thermal zone may be generated and/or maintained by at least one of the temperate control device and/or techniques previously described. A thermal zone having a known temperature (e.g., through measurement and/or through production of a known temperature), for example, may increase accuracy of a measurement of a physiological parameter level by the first sensor 240 as previously discussed.

FIGS. 12A-16 illustrate various electronic devices, such as a CCD (e.g., CCD 301), which may be employed as the CCD 16 (e.g., FIG. 1) or any other device discussed throughout the disclosure in accordance with an embodiment of the present invention. Although the CCD of FIGS. 12A-16 may be similar or used with the embodiments of FIGS. 2-11, it should be understood that the CCD of FIGS. 12A-16 may also include some or all of the same components and operate in a manner similar to that shown and described in the embodiments of FIG. 1. In addition, some or all of the features shown in FIGS. 1-11 may be combined in various ways and included in the embodiments shown in FIGS. 12A-16. Likewise, it should be understood that any of the features of the embodiments of FIGS. 12A-16 may be combined or otherwise incorporated into any of the other embodiments of FIGS. 12A-16 as well as any other embodiment herein discussed.

Figure 12B:
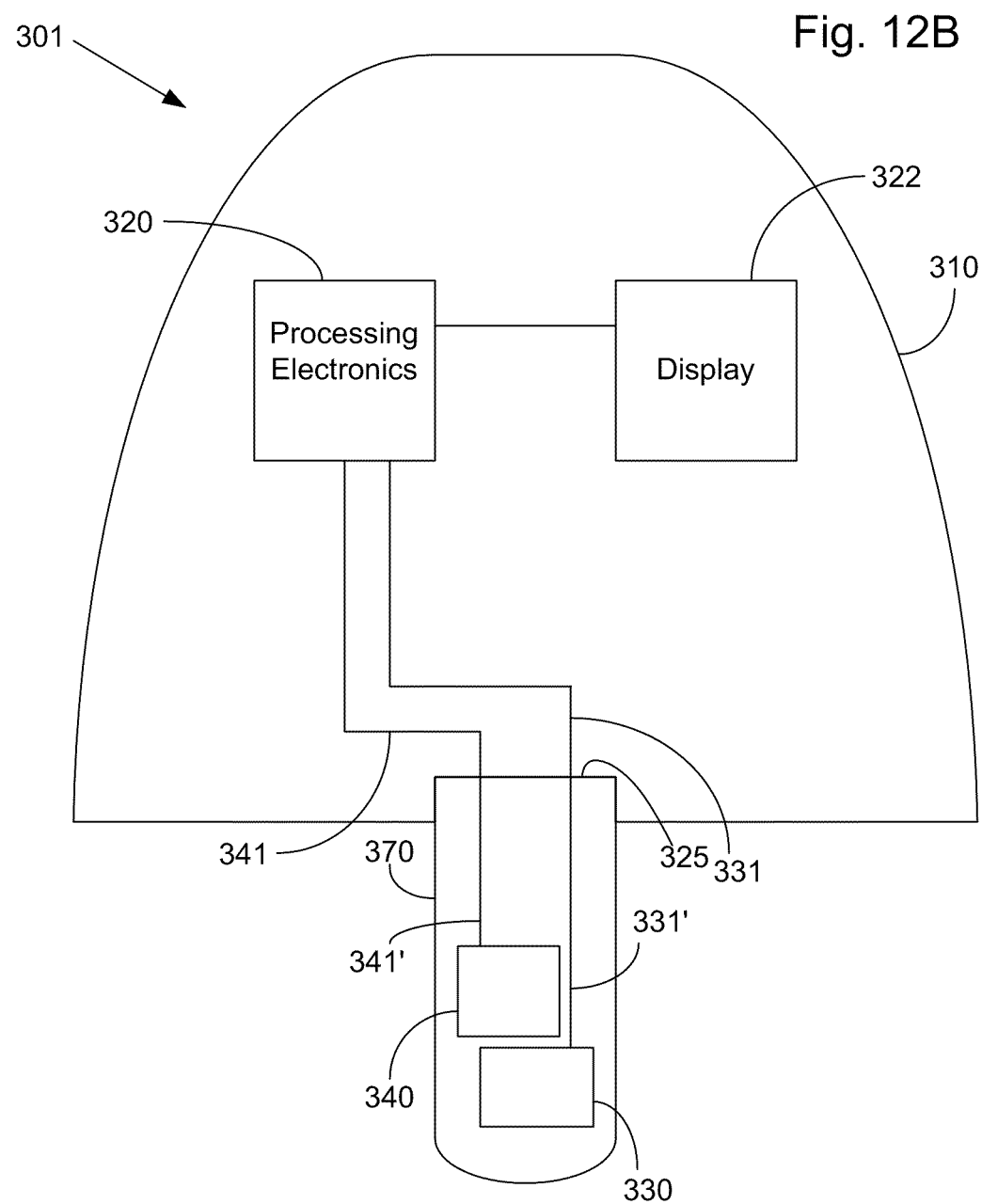

FIGS. 12A and 12B illustrate a monitoring system 300 according to an embodiment of the present invention. The monitoring system may include, but is not limited to, a CCD 301 and an external device 370 having a first sensor 330. In various embodiments, the CCD 301 may be similar to the CCD 101 discussed above (e.g., FIGS. 2-4) and/or the CCD 201 discussed above (e.g., FIGS. 9-11). The CCD 301 may include a housing 310 and a processor 320. In further embodiments, the CCD 301 may include a display device 322, which may be similar to the display device 122 (e.g., FIGS. 2-6).

The external device 370 may be a structure adapted to be removably connectable to the CCD 301. For example, the CCD 301 may include a receptacle 325, port, socket, or the like for receiving and/or supporting at least a portion of the external device 370, such as, but not limited to, an end 372 of the external device 370. As such, the external device 370 may allow for selective electronic disconnection and/or separation or engagement and/or electrical connection between the CCD 301 and the external device 370.

The external device 370 may include a first sensor 330, which may be similar to the first sensor (130 or 230) discussed with respect to FIGS. 2-11, for sensing a physiological parameter. Returning to FIGS. 12A and 12B, the CCD 301 may be configured for use with the external device 370 and the first sensor 330. For example, the CCD 301 and the external device 370 may be connectable directly, for example, at the receptacle 325 or through a connector (not shown), a wireless communication link, and/or the like. For example, the external device 370 may have an interconnect 331' for electrically connecting the first sensor 330 with an interconnect 331 in the CCD 301 to establish an electrical connection to the processor 320 (e.g., FIG. 12B) when the external device 370 is engaged, for example in the receptacle 325, with the CCD 301.

The external device 370 having the first sensor 340 may be a test strip, biosensing meter (e.g., similar to apparatus as described in U.S. Pat. No. 5,405,511, entitled "Biosensing Meter With Ambient Temperature Estimation Method and System," which is herein incorporated by reference in its entirety), or the like. The test strip may be for analyzing an analyte-containing sample, for example, by subjecting the sample to a glucose determination. In the following example, the analyte-containing sample being subjected to a glucose determination may be a drop of blood.

A test strip for a glucose determination may (or may not) include one or more reactants within a receptacle for receiving and/or testing the sample, where such reactants may comprise, but are not limited to, an enzyme, an electrolyte, a mediator, film formers, and a buffer. For instance, the enzyme may be, but is not limited to, glucose oxidase or glucose dehydrogenase; the buffer may be, but is not limited to, organic or inorganic buffer material; the electrolyte may be, but is not limited to, potassium chloride or sodium chloride; the mediator may be, but is not limited to, potassium ferricyanide; the film formers may comprise, but is not limited to, gelatin and/or propiofin. If the test cell is to be employed for a cholesterol concentration determination, the enzyme may be a cholesterol oxidase, with or without a cholesterol esterase additive. The buffer may be preferably inorganic and may include an electrolyte such as potassium chloride or sodium chloride. In this case, two mediators may be used, e.g., ferricyanide and quinone, and may be placed in the gelatin film.

Glucose determination may be performed as known in the art. According to one exemplary method, glucose determination may be performed by initially placing a sample of blood in a well of the test strip. The glucose within the sample may cause a forward reaction of potassium ferricyanide to potassium ferricyanide. The forward reaction may proceed to completion during an incubation period. A subsequent application of an excitation voltage to an electrode in the test strip may create a small current at an opposite electrode that may result from a reverse reaction of potassium ferricyanide back to potassium ferricyanide. The flow of electrons during the reverse reaction may be sensed and measured at a number of points and compared to a model or curve to determine glucose concentration. Any resultant glucose value may be adjusted to take into account an ambient temperature.

In some embodiments, the external device 370 may include a second sensor 340, which may be similar to the second sensor (140 or 240) discussed with respect to FIGS. 2-11. Returning to FIGS. 12A and 12B, the external device 370 may include an interconnect 341' for electrically connecting the second sensor 340 with an interconnect 341 in the CCD 301 to establish an electrical connection with the processor 320 (e.g., FIG. 12B).

Figure 13:
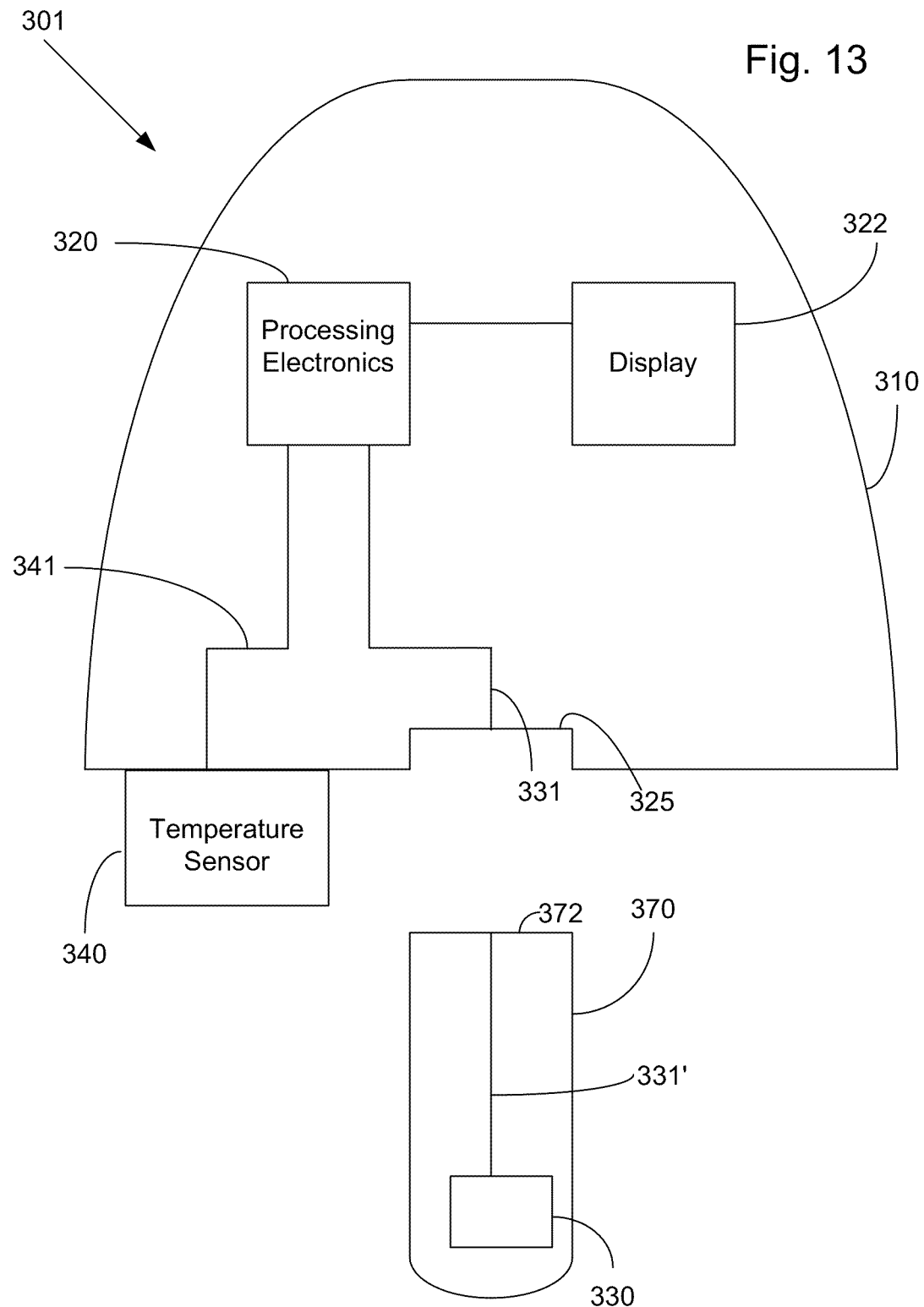
FIG. 13 illustrates a block diagram of a monitoring device in accordance with an embodiment of the present invention.
Figure 15:
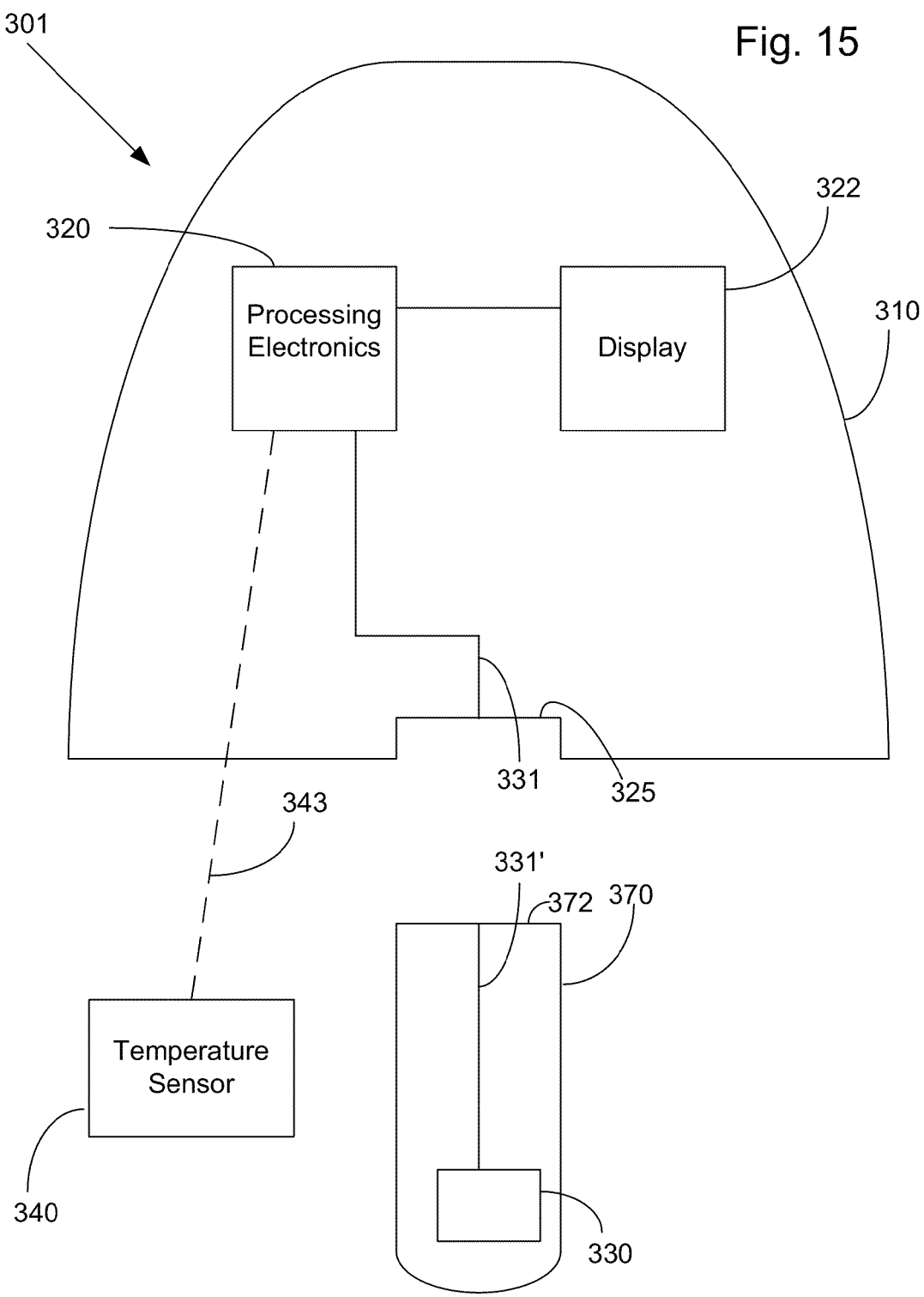
FIG. 15 illustrates a block diagram of a monitoring device in accordance with an embodiment of the present invention.

In other embodiments, such as the embodiment exemplified in FIG. 13, the second sensor 340 may be located on an external surface of the CCD 301 in a manner similar to at least one of the embodiments described above, for example, with respect to FIG. 7. In other embodiments, such as the embodiment exemplified in FIG. 14, the housing of the CCD 301 may include a chamber 312 in which the second sensor 340 may be located in a manner similar to at least one of the embodiments described above, for example, with respect to FIGS. 2-6. In other embodiments, such as the embodiment exemplified in FIG. 15, the second sensor 340 may be located separate and spaced apart from the CCD 301 in a manner similar to at least one of the embodiments described above, for example, with respect to FIGS. 9-11.

In other embodiments, such as the embodiment exemplified in FIG. 16, the housing 310 of the CCD 301 may include a portion extending away from the housing 310, such as a tab 316. The second sensor 340 may be located in or on the tab 316. In some embodiments, the tab 316 may have a size and/or a shape similar to a size and/or a shape of the external device 370 (e.g., the test strip).

In some embodiments, the second sensor 340 may be located at a position in or on the tab 316 to be at least partially in alignment (e.g., vertical alignment or horizontal alignment) with the first sensor 330 in a case where the external device 370 is connected with the CCD 301. For example, the second sensor 340 may be positioned along the tab 316 such that the second sensor 340 may align with the first sensor 330 in a case where the external device 370 is connected to the CCD 301.

As another example, the second sensor 340 may be positioned along the tab 316, and a user-patient may move the external device 370 so that the first sensor 330 may be in alignment with the second sensor 340. Accordingly, in such embodiments, the first sensor 330 and the second sensor 340 can be in contact or close to one another with minimal spacing between the first sensor 330 and the second sensor 330. This may allow the second sensor 340 to measure a temperature of a location that is approximate to a location of the first sensor 330. Furthermore, because the locations of the first sensor 330 and the second sensor 340 are located sufficiently away from and/or otherwise thermally insulated from heat-generating electronics (e.g., processor 320, display 322) within the CCD 301, a thermal effect of heat from the heat-generating electronics in the CCD 301 on the temperature(s) near the first sensor 330 and/or the second sensor 340 may be minimized.

Although embodiments of the present invention are directed to a first sensor and a second sensor for use with a CCD, various embodiments are applicable to other devices other than a CCD. For example, embodiments of the present invention can be used with, but is not limited to, medical devices, pumps (e.g., insulin), or any other device configured to analyze, monitor, or treat a user-patient based on a physiological parameter. In addition, embodiments of the present invention can be used with, but is not limited to any device that has a temperature (e.g., internal temperature) that differs from ambient temperature.

Although embodiments of the present invention are described in the context of glucose monitors used in the treatment of diabetes, the embodiments of the invention are applicable to a wide variety of patient treatment programs where a physiological parameter is monitored. For example, embodiments of the present invention can be used, but is not limited, to determine the status and/or levels of a variety of characteristics including those associated with agents such as hormones, cholesterol, medication concentrations, pH, oxygen saturation, viral loads (e.g., HIV), and/or the like.

The embodiments disclosed herein are to be considered in all respects as illustrative, and not restrictive of the invention.

The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A monitoring system for measuring a physiological parameter, the system comprising:
   a housing having electronics, the electronics including heat-generating electronics, a first sensor and a second sensor;
   the first sensor configured to measure a sensed amount of a physiological parameter and to generate a first signal based on the sensed amount of the physiological parameter measured by the first sensor; and
   the second sensor electrically connected to the electronics in the housing and configured to measure a temperature and to generate a second signal based on the temperature measured by the second sensor;
   the heat-generating electronics comprising a processor configured to determine an overall amount of the physiological parameter based on the first signal generated from the first sensor and the second signal generated from the second sensor;
   the second sensor held by a support structure, the second sensor thermally insulated from the heat-generating electronics and the first sensor and the second sensor are non-abutting; and
   a thermal insulation material arranged to thermally insulate the second sensor from the heat-generating electronics and the first sensor, while the second sensor remains electrically connected to the heat-generating electronics in the housing, wherein the thermal insulation material is configured to thermally insulate the second sensor so that the temperature measured by the second sensor is thermally insulated from heat emitted by the first sensor, and the thermal insulation material is arranged between the first sensor and the second sensor through all direct line-of-sight convection paths from the first sensor to the second sensor such that the temperature measured by the second sensor is isolated from the heat emitted by the first sensor through all direct line-of-sight convection paths.

2. The system of claim 1, wherein the physiological parameter comprises a concentration of blood glucose.

3. The system of claim 1, wherein the thermal insulation material surrounds at least a portion of the second sensor, the thermal insulation material is adapted to thermally insulate the second sensor from heat generated by the heat-generating electronics.

4. The system of claim 1,
   the housing having a chamber, the second sensor arranged within the chamber;
   the chamber being coupled to the thermal insulation material; and
   the chamber sufficiently located away from the heat-generating electronics to minimize an affect of the heat-generating electronics on the temperature measured by the second sensor.

5. The system of claim 4,
   the chamber located at a location corresponding to approximately a furthest distance within the housing from the heat-generating electronics.

6. The system of claim 4,
   the chamber located at a location corresponding to a coolest portion of the housing during operation of the monitoring system.

7. The system of claim 1, wherein the thermal insulation material surrounds at least a portion of the second sensor, the thermal insulation material adapted to thermally insulate the second sensor from at least one of heat generated by the heat-generating electronics and air external to the housing; and
   the housing has a chamber, the support structure arranged within the chamber of the housing.

8. The system of claim 1, the second sensor arranged external to the housing.

9. The system of claim 8, the second sensor attached to an external surface of the housing.

10. The system of claim 8, the second sensor located separate and spaced apart from the housing.

11. The system of claim 1, wherein the first sensor is arranged within the housing.

12. The system of claim 1,
    the first sensor configured to measure the sensed amount of the physiological parameter at a location having a local temperature; and
    the second sensor adapted to be positioned relative to the housing at a location at which the temperature measured by the second sensor is closer to the local temperature than a temperature of a heat source emitted by the heat-generating electronics.

13. The system of claim 1, the system further comprising:
    a heat-conductive material adapted to transfer heat away from at least one of a portion of the housing containing the heat-generating electronics and a portion of the housing containing the second sensor to raise or lower a temperature within the housing measured by the second sensor.

14. The system of claim 13, wherein the heat-conductive material comprises a heat sink.

15. The system of claim 1, the system further comprising:
    a heat-conductive material adapted to transfer ambient temperature to at least one of a portion of the housing containing the heat-generating electronics and a portion of the housing containing the second sensor to raise or lower a temperature within the housing measured by the second sensor.

16. The system of claim 1, the housing having an opening for allowing air external to the housing to flow to at least one of a portion of the housing containing the heat-generating electronics and a portion of the housing containing the second sensor to raise or lower a temperature within the housing measured by the second sensor.

17. The system of claim 1, the system further comprising:
    a ventilation device for providing air external to the housing to at least one of a portion of the housing containing the heat-generating electronics and a portion of the housing containing the second sensor to raise or lower a temperature within the housing measured by the second sensor.

18. The system of claim 1, the system further comprising:
    a ventilation device for transferring air away from within at least one of a portion of the housing containing the heat-generating electronics and a portion of the housing containing the second sensor to outside the housing to raise or lower a temperature within the housing measured by the second sensor.

19. The system of claim 1, the processor further configured to provide an indicator based upon at least one of the first signal exceeding a threshold range and the second signal exceeding a threshold range.

20. The system of claim 1, the system further comprising:
a removable support structure for removable connection with the housing, the removable support structure for supporting the first sensor.

21. The system of claim 20, wherein the removable support structure comprises a test strip.

22. The system of claim 20, the housing having a receptacle for receiving at least a portion of the removable support structure and for providing an electrical connection for electrically connecting the removable support structure and the housing.

23. The system of claim 22, wherein the portion of the removable support structure receivable by the receptacle is an end of the removable support structure.

24. The system of claim 20, the removable support structure for supporting the second sensor.

25. The system of claim 20,
the removable support structure configured to measure the sensed amount of the physiological parameter at a location along the removable support structure; and
the second sensor locatable at a position to be adjacent with the location on the removable support structure.

26. The system of claim 25,
the housing having a portion extending away from the housing; and
the second sensor located along the portion extending away from the housing to be adjacent with the location on the removable support structure.

27. The system of claim 1, the second sensor sufficiently located from the heat-generating electronics to minimize an affect of the heat-generating electronics on the temperature measured by the second sensor.

28. The system of claim 27, the second sensor located at a location corresponding to approximately a furthest distance within the housing from the heat-generating electronics.

29. The system of claim 27, the second sensor located at a location corresponding to a coolest portion of the housing during operation of the monitoring system.

30. The monitoring system of claim 1, wherein the second sensor being in contact with the support structure and the support structure being in contact with a thermal insulation and the thermal insulation being in contact with the housing such that:
the second sensor fails to contact the thermal insulation; and
the support structure fails to contact the housing.

31. The monitoring system of claim 30, wherein the support structure forms a tray shape and the support structure has an opening to outside the housing.

32. The system of claim 1, wherein the support structure and the housing are separated by a first thermal insulating material that is made of different material than the housing.

33. The system of claim 32, further comprising a second thermal insulating material that separates the support structure and the housing.

34. The system of claim 1, further comprising at least two mounting structures, wherein the first sensor and the second sensor are mounted on different mounting structures.

35. The system of claim 1, wherein the first sensor held by a second support structure such that the second support structure is spaced apart from the support structure holding the second sensor.

36. The system of claim 1, wherein the thermal insulation material is arranged between the second sensor and a heat-emitting portion of the first sensor, the thermal insulation material is configured to thermally insulate the second sensor from the heat-emitting portion of the first sensor such that the temperature measured by the second sensor is substantially independent from the heat emitted by the heat-emitting portion of the first sensor.

37. The system of claim 1, wherein:
the second sensor is configured to sense an ambient temperature at approximately a location where enzyme reaction occurs while the second sensor is insulated from the first sensor by the thermal insulation material; and
the first sensor measures the sensed amount of the physiological parameter at approximately the location where enzyme reaction occurs.

38. The system of claim 1, wherein the thermal insulation material is directly connected to only one of the first sensor or the second sensor.

39. A method of manufacturing a monitoring system for measuring a physiological parameter, the method comprising:
providing a housing having electronics, the electronics including heat-generating electronics, a first sensor and a second sensor;
connecting the first sensor with the housing, the first sensor for measuring a sensed amount of a physiological parameter and for generating a first signal based on the sensed amount of the physiological parameter measured by the first sensor;
arranging the second sensor to be held by a support structure, the second sensor for measuring a temperature and for generating a second signal based on the temperature measured by the second sensor, and electrically connecting the second sensor to the electronics in the housing;
determining an overall amount of the physiological parameter based on the first signal generated from the first sensor and the second signal generated from the second sensor; and
thermally insulating, using a thermal insulation material, the second sensor from the heat-generating electronics and the first sensor, and the first sensor and the second sensor are non-abutting; and
placing the thermal insulation material to thermally insulate the second sensor from the first sensor and the heat-generating electronics that are located within the housing, while the second sensor remains electrically connected to the heat-generating electronics in the housing, wherein the thermal insulation material is configured to thermally insulate the second sensor so that the temperature measured by the second sensor is thermally insulated from heat emitted by the first sensor, and the thermal insulation material is arranged between the first sensor and the second sensor through all direct line-of-sight convection paths from the first sensor to the second sensor such that the temperature measured by the second sensor is isolated from the heat emitted by the first sensor through all direct line-of-sight convection paths.

40. A medical device for measuring a parameter, the device comprising:
a medical monitoring or treatment device configured to provide a monitoring or treatment operation on a user, the medical monitoring or treatment device configured to receive a first signal from a parameter sensor configured to detect an amount of a physiological parameter, the first signal being based on the amount of the physiological parameter detected by the parameter sensor;

a temperature sensor configured to measure a temperature and to generate a second signal based on the temperature measured by the temperature sensor;

wherein the parameter sensor and temperature sensor are non-abutting;

the temperature sensor held by a support structure and the temperature sensor electrically connected to a computing element;

a computing element configured to determine an overall amount of the physiological parameter based on the first signal and the second signal; and the temperature sensor thermally insulated from heat produced within the medical monitoring or treatment device during use of the medical monitoring or treatment device; and a thermal insulation material arranged to thermally insulate the temperature sensor from the heat-generating electronics and the parameter sensor, while the temperature sensor remains electrically connected to the computing element, wherein the thermal insulation material is configured to thermally insulate the temperature sensor so that the temperature measured by the temperature sensor is thermally insulated from heat emitted by the parameter sensor, and the thermal insulation material is arranged between the parameter sensor and the temperature sensor through all direct line-of-sight convection paths from the parameter sensor to the temperature sensor such that the temperature measured by the temperature sensor is isolated from the heat emitted by the parameter sensor through all direct line-of-sight convection paths.

* * * * *